United States Patent [19]
Ohki et al.

[11] Patent Number: 5,901,703
[45] Date of Patent: *May 11, 1999

[54] MEDICINE ADMINISTERING DEVICE FOR NASAL CAVITIES

[75] Inventors: Hisatomo Ohki; Shigemi Nakamura, both of Isesaki; Kazunori Ishizeki, Fujimi; Akira Yanagawa, Yokohama, all of Japan

[73] Assignees: Unisia Jecs Corporation, Atsugi; Dott Limited Company, Yokohama, both of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/687,432

[22] PCT Filed: Feb. 6, 1995

[86] PCT No.: PCT/JP96/00242

§ 371 Date: Aug. 9, 1996

§ 102(e) Date: Aug. 9, 1996

[87] PCT Pub. No.: WO96/24400

PCT Pub. Date: Aug. 15, 1996

[30] Foreign Application Priority Data

| Feb. 6, 1995 | [JP] | Japan | 7/42306 |
| Feb. 6, 1995 | [JP] | Japan | 7-42309 |
| Apr. 12, 1995 | [JP] | Japan | 7/111252 |

[51] Int. Cl.⁶ .................................................. A61M 15/00
[52] U.S. Cl. ............................. 128/203.12; 128/203.22; 128/207.18; 128/200.14; 128/200.22; 128/203.15
[58] Field of Search ................... 128/203.12, 203.22, 128/207.18, 200.14, 200.22, 203.15; 604/48, 73, 75, 212, 316; 239/309, 327, 328, 329

[56] References Cited

U.S. PATENT DOCUMENTS

| 3,906,950 | 9/1975 | Cocozza | 128/203.15 |
| 3,949,751 | 4/1976 | Birch et al. | 128/203.15 |
| 4,249,526 | 2/1981 | Dean et al. | 128/203.15 |
| 4,884,565 | 12/1989 | Cocozza | 128/203.15 |
| 4,889,114 | 12/1989 | Kladders | 128/203.15 |
| 4,995,385 | 2/1991 | Valentini et al. | 128/203.15 |
| 5,263,475 | 11/1993 | Altermatt et al. | 128/203.15 |
| 5,351,683 | 10/1994 | Chiesi et al. | 128/203.15 |
| 5,619,985 | 4/1997 | Ohki et al. | |
| 5,647,349 | 7/1997 | Ohki et al. | |

FOREIGN PATENT DOCUMENTS

| 0303844 | 2/1989 | European Pat. Off. | 128/203.15 |
| 59-34267 | 2/1984 | Japan. | |
| 3003998 | 8/1994 | Japan. | |
| 2151491 | 7/1985 | United Kingdom | 128/203.15 |
| WO 91/02558 | 3/1991 | WIPO | 128/203.12 |
| WO 92/21404 | 12/1992 | WIPO | 128/203.12 |

*Primary Examiner*—Mickey Yu
*Assistant Examiner*—Dinh X. Nguyen
*Attorney, Agent, or Firm*—Foley & Lardner

[57] ABSTRACT

A capsule holder is provided with a capsule accommodating hole and a supplying valve. A pump section having a sucking valve is provided at the air inflow-side of the capsule holder, while a medicine spraying section having two medicine passages diverging from the capsule accommodating hole and spraying holes is provided at the air outflow-side of the capsule holder. A perforator is housed in the medicine spraying section. A capsule is accommodated in the capsule accommodating hole, and through-holes are formed in the capsule with the perforator, upon which the medicine within the capsule can be administered to the left and right nasal cavities of a patient under the action of air from the pump section. Additionally, a spreading chamber is provided to be formed at the downstream side of the capsule accommodating hole. Air and the medicine from the capsule can be effectively mixed with each other by virtue of this spreading chamber, so that the medicine can be administered to the left and right nasal cavities of the patient at a uniform mixing degree.

11 Claims, 20 Drawing Sheets

MEDICINE ADMINISTERING DEVICE FOR NASAL CAVITIES

FIELD OF THE INVENTION

The present invention relates to a medicine administering device suitable for administering powder-state medicine, for example, into the nasal cavities of a patient.

BACKGROUND TECHNIQUE

In general, a method of curing by administering powder-state medicine through the nasal cavities can be employed for a patient with nasal allergy, asthma and the like. In this curing method, the powder-state medicine filled in a capsule is administered into the nasal cavities by using a medicine administering device for nasal cavities.

One device that may be used for this curing method is disclosed in Japanese Patent Provisional Publication No. 59-34267 (referred hereinafter to as a conventional technique).

In the device according to this conventional technique, a pump section is disposed at the air inflow-side of a cylindrical member. The above-mentioned cylindrical member is formed at its air outflow-side with a concave-shaped section to which a capsule is to be inserted. A tip end section is fitted to the concave-shaped section so as to form a capsule accommodating section. An air introduction passage is formed from the capsule accommodating section to the pump section. Additionally, a valve mechanism is disposed at the other-side of the above-mentioned pump section. By this valve mechanism, air is supplied through the air introduction passage when the pump section is pressed, while air is sucked into the pump section from outside when the pump section is restored. Furthermore, the device is provided with a cap fitted to the above-mentioned cylindrical member and the tip end section. The cap is provided thereinside with an axially extending pin, and arranged such that a hole is formed in the capsule by installing the cap under a condition in which the concave-shaped section of the above-mentioned cylindrical member and the tip end section having an opened section are fitted with each other.

In the thus arranged conventional technique, first in order to form the hole in the capsule in preparation of administration, the tip end section is fitted to install the capsule in the accommodating section after the capsule filled with the powder-state medicine is inserted in the concave-shaped section. Then, the cap is installed so that the pin is inserted in the opened section of the tip end section, so that holes are formed at axially opposite sides of the capsule under the action of the pin.

Subsequently, in order to administer the medicine, the cap is removed from the cylindrical member. The tip end section is inserted into one of the nasal cavities of the patient, and then the pump section is pressed, so that air from the pump section flows in the capsule through the air introduction passage. The medicine within the capsule is transferred to the nasal cavities of the patient through the opened section. By repeating insertion of the device to the nasal cavities alternately in turn, administration of the medicine is accomplished.

Additionally, in the conventional technique, administration of the medicine to the nasal cavity is made alternately to the left and right nasal cavities, and therefore a clearance is formed between the capsule accommodating section and the capsule to prevent all of the medicine within the capsule from being administered only upon one pressing action to the pump section. An arrangement is made such that the medicine within the capsule is administered for one nasal cavity upon about four actions.

Also, since the medicine administration to the nasal cavity is made for each of the nasal cavities in the above-mentioned conventional technique, it is necessary to repeat the pressing action to the pump section and the inserting action of the cylindrical member into the nasal cavity, so that administering medicine is troublesome.

Additionally, since formation of the hole in the capsule is carried out by installing the detachable cap to the cylindrical member, the device cannot be used as a medicine administering device if the cap is lost.

Further, the powder-state medicine unavoidably drops to the pump section during hole formation. In this case, the amount of the medicine within the capsule drops below a predetermined amount, so that a necessary amount of the medicine cannot be administered to the patient and so that the device requires frequent cleaning to remove the medicine that has dropped into the pump section.

Furthermore, medicine may reach the nasal cavities of the patient without sufficient mixing between the medicine and air during the medicine administration, thereby reducing medicine administration efficiency.

DISCLOSURE OF THE INVENTION

The present invention has been made in view of a variety of problems in the above-mentioned conventional technique, and is intended to provide a medicine administering device by which medicine can be administered with simple medicine administration actions.

The medicine administering device, for nasal cavities, according to the present invention is comprised of a capsule holding section for holding a capsule in which powder-state medicine is filled; a pump section connected to the above-mentioned capsule holding section to supply air toward the capsule in the capsule holding section; a medicine spraying section connected to the above mentioned capsule holding section and having two medicine passages which diverge and have respective tip ends serving as independent spraying holes, to spray the medicine within the capsule into left and right nasal cavities of a patient under the action of air supplied from the pump section; and a perforator including a pin which is configured to be movable to form a through-hole in the capsule in the above-mentioned capsule holding section.

Accordingly, to form a hole, the pin of the perforator is moved to the capsule side after the capsule is held in the capsule holding section, and then through-holes are formed in the capsule by the tip end of the pin. To administer medicine, air is supplied from the pump section, and this air flows through the inside of the capsule through the formed through-holes and is transferred together with the medicine from the capsule through the respective medicine passages of the medicine spraying section from the left and right spraying holes to the respective left and right nasal cavities. By this, the medicine can be simultaneously administered to the left and right nasal cavities of the patient.

Additionally, an axial dimension of the capsule accommodating hole formed in the capsule holding section is slightly smaller than an axial dimension of the capsule. The capsule can be securely fixed and accommodated in the capsule accommodating hole, and the capsule hole can be tightly contacted with the air inflow-side and the air outflow-side. Accordingly, air from the pump section can stream into the capsule during the medicine administration, while effectively ejecting the medicine.

Further, a medicine trapping section is formed between the capsule holding section and the pump section. The medicine dropping into the pump section can be trapped by the medicine trapping section during the hole formation. This trapped medicine can be transferred together with the medicine in the capsule into the left and right nasal cavities of the patient through the capsule holding section and the medicine spraying section under the action of air from the pump section.

Additionally, a seal material is disposed in the medicine spraying section to allow the pin of the perforator to slide relative to each of the above-mentioned medicine passages to maintain a powder-tight seal. Air supplied from the pump section is prevented from flowing through the capsule holding section into the perforator side during the medicine administration.

Additionally, a capsule ejecting tool is disposed in the capsule holding section in a manner to be axially displaceable. The empty capsule can be pushed out from the capsule holding section by operating the capsule ejecting tool after the medicine administration.

Further, the medicine passages of the medicine spraying section respectively have straight sections which serve as acceleration passages. Flow-regulating characteristics and straight advancing characteristics are enhanced in the passing medicine by these acceleration passages so that the medicine can be forcibly ejected toward the nasal cavities of the patient in an accelerated state.

Additionally, a large-diameter spreading chamber is disposed between the accommodating hole and each medicine passage. Air supplied from the pump section and the medicine are well mixed with each other in the spreading chamber during the medicine administration, so that this air mixed with the medicine can be simultaneously transferred to the left and right nasal cavities of the patient through each medicine passage.

Further, by arranging that the spreading chamber has an air outflow-side which is formed as a small-diameter hole section, air streams collide with each other in the spreading chamber, thereby uniformizing the mixing degree of the medicine in air.

Furthermore, the medicine spraying section is formed of a material having an elasticity. Nonuniformity in distance between the left and right nasal cavities according to difference among individuals can be achieved.

DETAILED DESCRIPTION OF THE PREFERRED EMBODIMENTS

Figure 1:
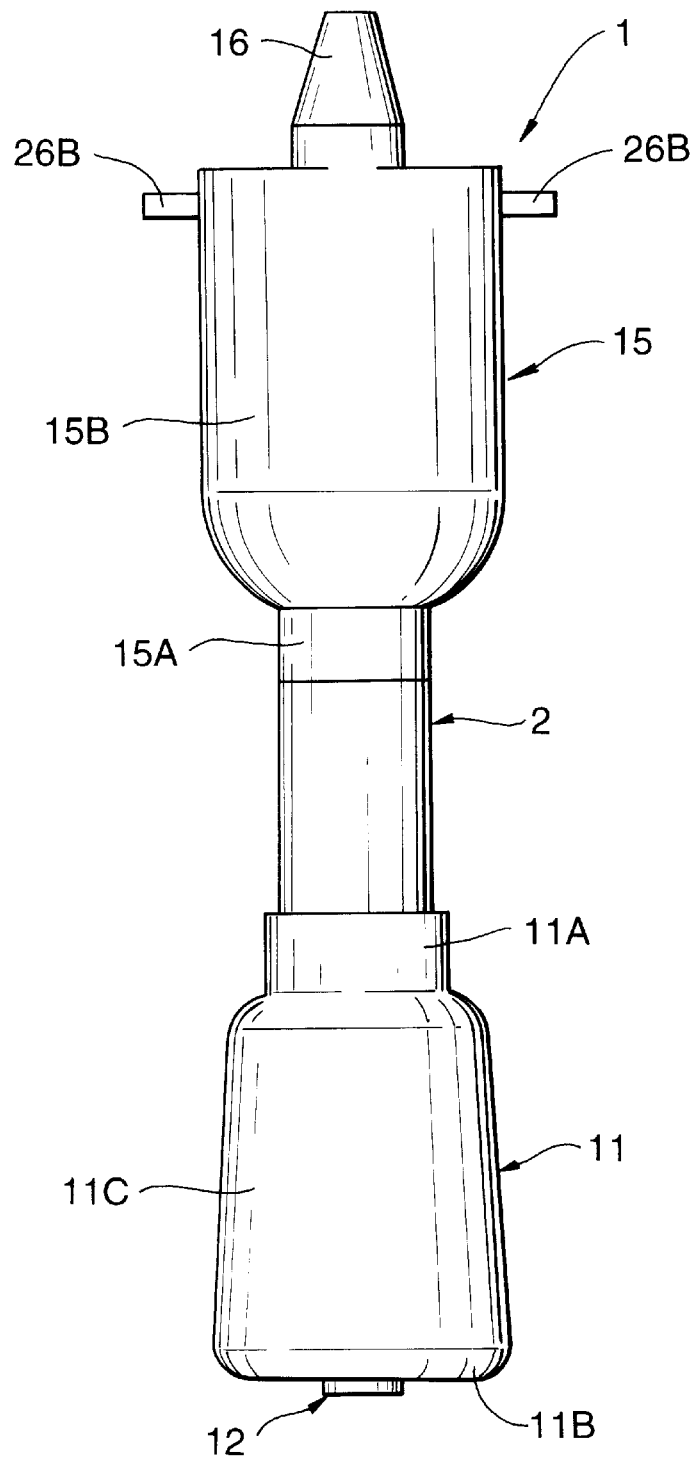
FIG. 1 is a side view showing a medicine administering device for nasal cavities, according to a first embodiment.

Hereinafter, embodiments of the present invention will be discussed with reference to the drawings.

First, a first embodiment of a medicine administering device for nasal cavities, according to the present invention will be discussed with reference to FIGS. 1 to 8.

In the drawings, 1 denotes a medicine administering device for nasal cavities. The medicine administering device 1 for nasal cavities is generally comprised of a capsule holder 2 constituting a capsule holding section located at an axial center to support a capsule K in cooperation with a medicine spraying section 15 which will be discussed after; a pump section 11 disposed to be located at an air inflow-side of the capsule holder 2 so as to supply air toward the capsule K in the capsule holder 2; the medicine spraying section 15 disposed to be located at an air outflow-side of the above-mentioned capsule holder 2 and constituting the capsule holding section at a part thereof in cooperation with the capsule holder 2, in which medicine spraying is carried out through the medicine spraying section 15 into left and right nasal cavities of a patient; and a perforator 25 disposed within the medicine spraying section 15 as to form holes in the capsule K accommodated in the capsule holder 2. The capsule holder 2 is integral with the pump section 11, while the capsule holder 2 is detachable from the medicine spraying section 15.

2 denotes the capsule holder constituting the capsule holding section. The capsule holder 2 is formed of a resin material and formed into the small-sized cylinder shape. The axial other side (air outflow-side) of the capsule holder 2 is formed at the outer peripheral surface with an external thread portion 3 and at its inner periphery with a one-side capsule hole 4. The one-side capsule hole 4 constitutes a capsule accommodating hole 5 upon being connected with an other-side capsule hole 18 which is in the medicine spraying section 15 and will be discussed after. An axial one-side (air inflow-side) of the above-mentioned one-side capsule hole 4 is formed with an air supply passage 6 through which air from the pump section 11 is supplied, a supplying valve chamber 7 which has a relatively large diameter and is in communication with the air supply passage 6, and a capsule inflow-side passage 8 which has a relatively small diameter and is opened from the supplying valve chamber 7 to the capsule hole 4. Further, the above-mentioned supplying valve chamber 7 is formed therein with a medicine complementing section 30 which will be discussed after.

9 denotes a supplying valve 9 which includes a valve member 10 disposed in the above-mentioned supplying valve chamber 7. The valve member 10 is adapted to open when air is supplied from the pump section 11, and to be seated during air sucking thereby closing the air supply passage 6.

11 denotes the pump section disposed on the air inflow-side of the capsule holder 2. The pump section is formed of a rubber material and formed into the shape of a cylinder having a closed bottom, including an opened section 11A, a bottom section 11B and a pressing section 11C constituted by a peripheral surface. The above-mentioned capsule holder 2 is hermetically fitted at its one side outer peripheral surface to the opened section. A sucking valve 12 which will be discussed after is installed to the central part of the bottom section 11B.

12 denotes the sucking valve which is formed at the bottom section 1 1B of the pump section 11 and includes a sucking passage 13 located at the central part of the sucking valve, and a valve member 14 which is adapted to open or close the sucking passage 13. The valve member 14 is adapted to close when air is supplied from the pump section 11 and opens during air sucking to suck air in the pump section 11 from outside.

15 denotes the medicine spraying section disposed on the air outflow-side of the capsule holder 2. The medicine spraying section 15 is formed of a resin material and formed into the external shape of a cylinder wherein the axial one-side constitutes a relatively small diameter section 15A having a diameter equal to that of the capsule holder 2 while the other-side constitutes a relatively large diameter section 15B. A pair of nasal cavity inserting sections 16 are formed projecting from the large diameter section 15B. The small diameter section 15A is formed at its inner peripheral side with an internal thread portion 17 which is engageable with the external thread portion 3 of the above-mentioned capsule holder 2. The small diameter section 15A is formed at its end face with the other-side capsule hole 18 which constitutes the capsule accommodating hole 5 in cooperation with the one-side capsule hole 4. A section of the medicine spraying section 15, located opposite the other-side capsule hole 18, is formed with a capsule inflow-side passage 19 in communication with the other-side capsule hole 18. Two elongate medicine passages 20 extend generally in U-shape upon diverging from the capsule outflow-side passage 19. The tip end side of each medicine passage 20 constitutes an independent spraying hole 21 located in the nasal cavity inserting section 16.

Here, the above-mentioned medicine passages 20 include respectively diverging passage sections 20A, each of which is diverging left or right from the capsule outflow-side passage 19, and further include respectively straight passage sections 20B, each of which extends from each diverging passage section 20A to the nasal cavity inserting section 16 so as to constitute an acceleration passage. Each straight passage section 20B is formed straight and elongated and therefore can provide flow-regulating characteristics and straight advancing characteristics to the medicine passing through the straight passage section 20B and to the air flow from the pump section 11, so that the medicine can be forcibly ejected in its accelerated state through the spraying hole 21.

Furthermore, a perforator installing hole 22 is formed between the medicine passages 20 extending axially in the medicine spraying section 15 in order that the perforator 25 is accommodated axially in the hole 22, in which the hole 22 includes a pair of elongate holes 22A (See FIG. 3) which are radially located and axially extend. A part of the perforator installing hole 22 at a location near the capsule outflow-side passage 19 includes a pin inserting hole 23 through which a member 27 passes, and a seal installation step section 24 to which a rubber seal 29 is installed, the step section 24 being located between the pin inserting hole 23 and each medicine passage 20. The pin inserting hole 23 and the seal installation step section 24 are formed coaxially with each other.

Figure 2:
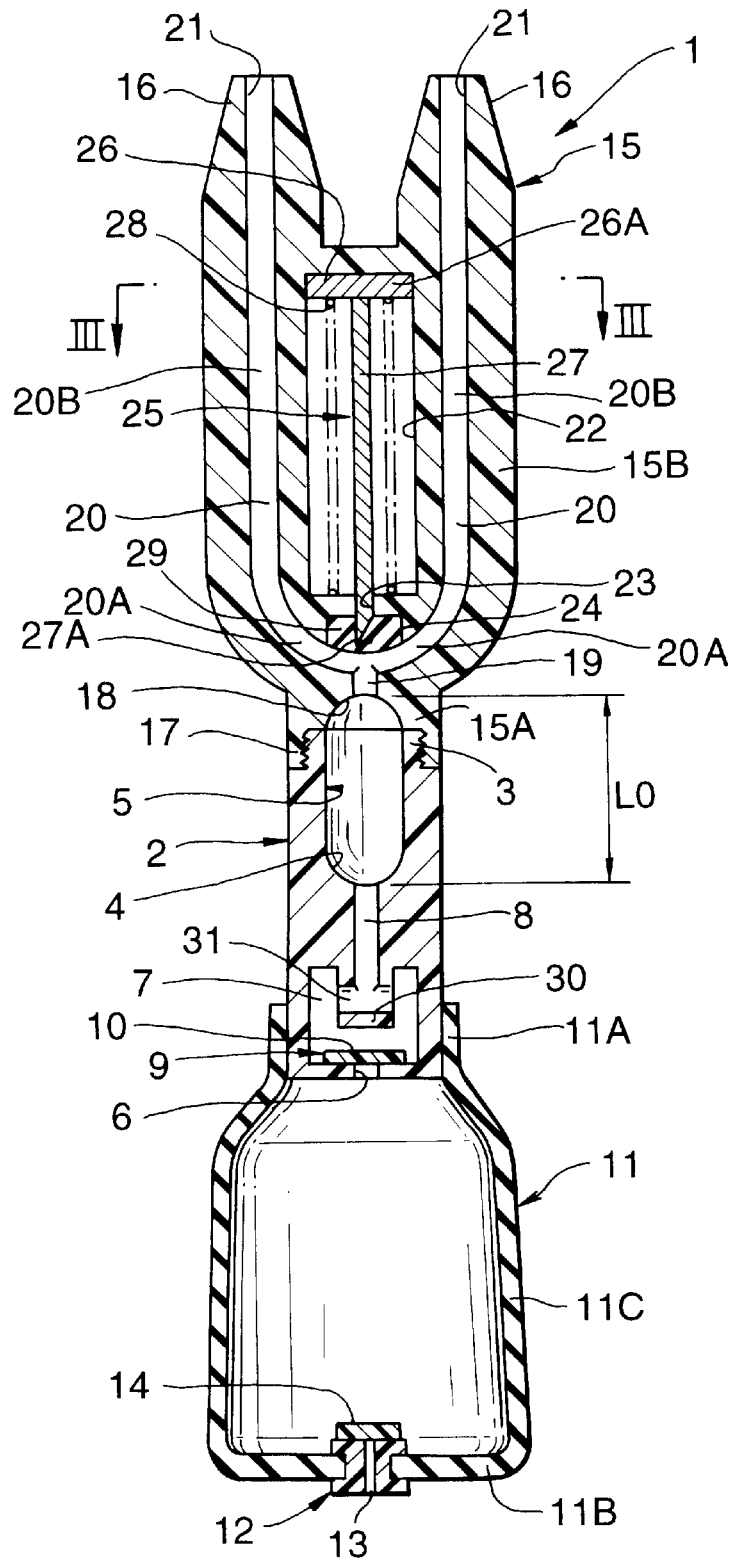
FIG. 2 is a longitudinal sectional view showing the medicine administering device for nasal cavities, according to the first embodiment.
Figure 3:
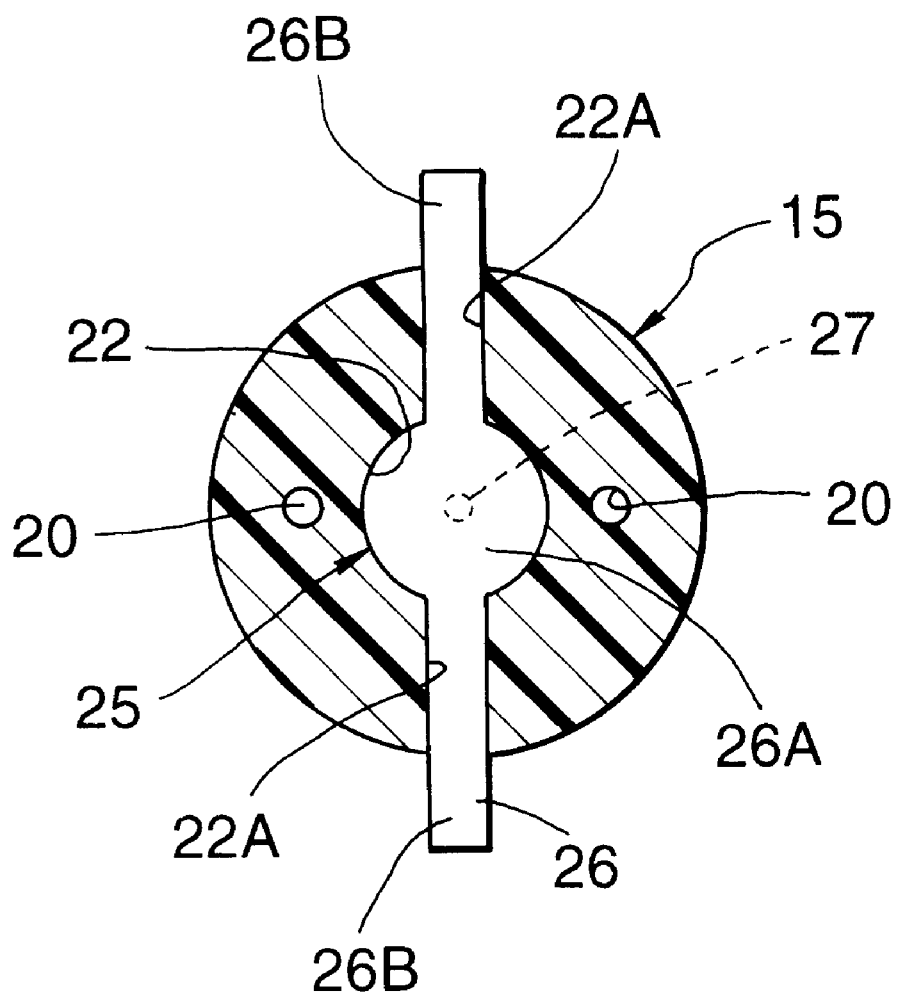
FIG. 3 is a transverse sectional view as viewed from the direction III—III indicated by an arrow in FIG. 2.

Here, as shown in FIG. 2, the capsule accommodating hole 5 is formed under cooperation of the one-side capsule hole 4 and the other-side capsule hole 18 by causing the external thread portion 3 of the capsule holder 2 and the internal thread portion 17 of the medicine spraying section 15 to be engaged with each other. At this time, the capsule K can be securely axially fixed in the capsule accommodating hole 5 by arranging such that the axial dimension LO of the capsule accommodating hole 5 is slightly smaller than the axial dimension LK of the capsule K.

Figure 4:
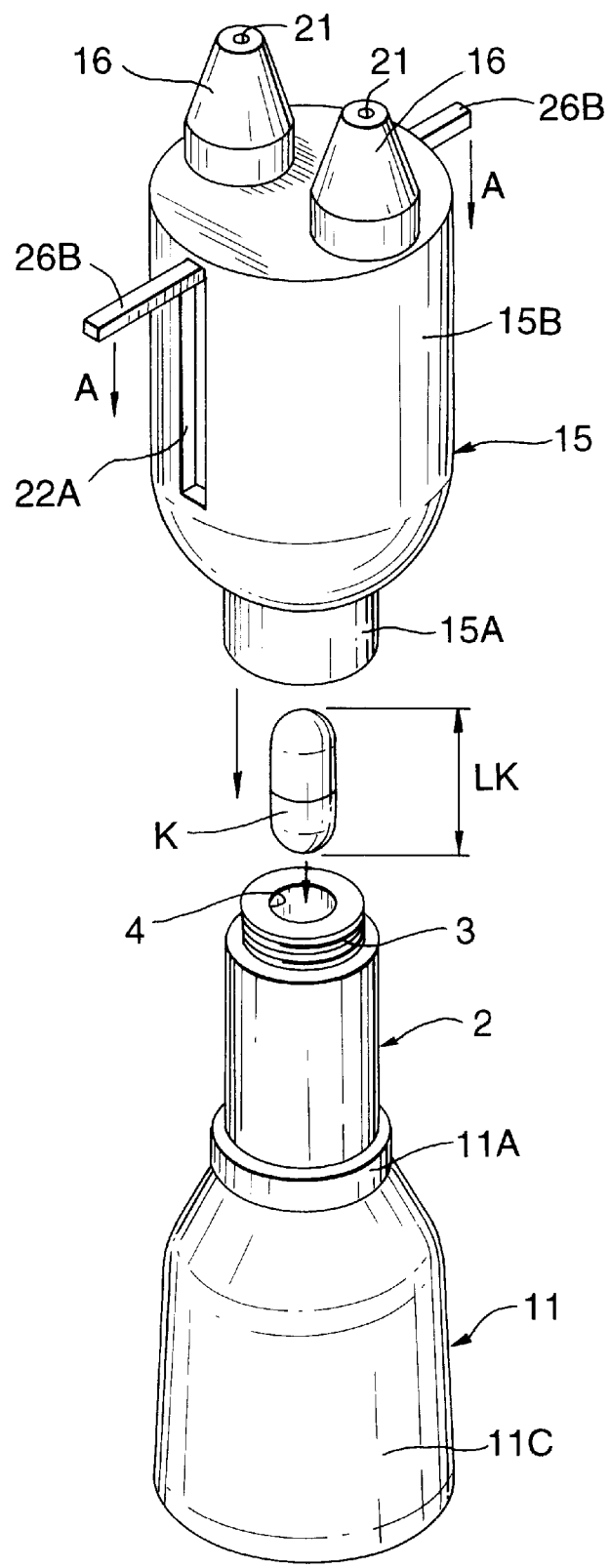
FIG. 4 is an exploded perspective view showing a state established before a capsule is accommodated in the medicine administering device for nasal cavities.

25 denotes the perforator disposed in the perforator installing hole 22 of the medicine spraying section 15. The perforator 25 includes a pusher 26 (See FIG. 3) formed integral to have a disc section 26A and a pair of projecting sections 26B, which radially project from the disc section 26A and are respectively fitted in the elongate holes 22A, a pin 27 which is fixed at its base end-side to the central part of the disc section 26A of the pusher 26 and has a hole forming section 27A which extends toward the axial one-side forming an inclined cutting needle at its tip end side, and a spring 28 disposed in the above-mentioned perforator installing hole 22 to bias the disc section 26A of the above-mentioned pusher 26 in an extending direction so as to push the above-mentioned pusher 26 toward the axial one side. The projecting sections 26B of the above-mentioned pusher 26 project respectively into the elongate holes 22A of the perforator installing hole 22 in an axially replaceable manner as shown in FIG. 4. When the pin 27 is inserted in the pin inserting hole 23, the front end hole forming section 27A is located within the rubber seal 29.

Figure 6:
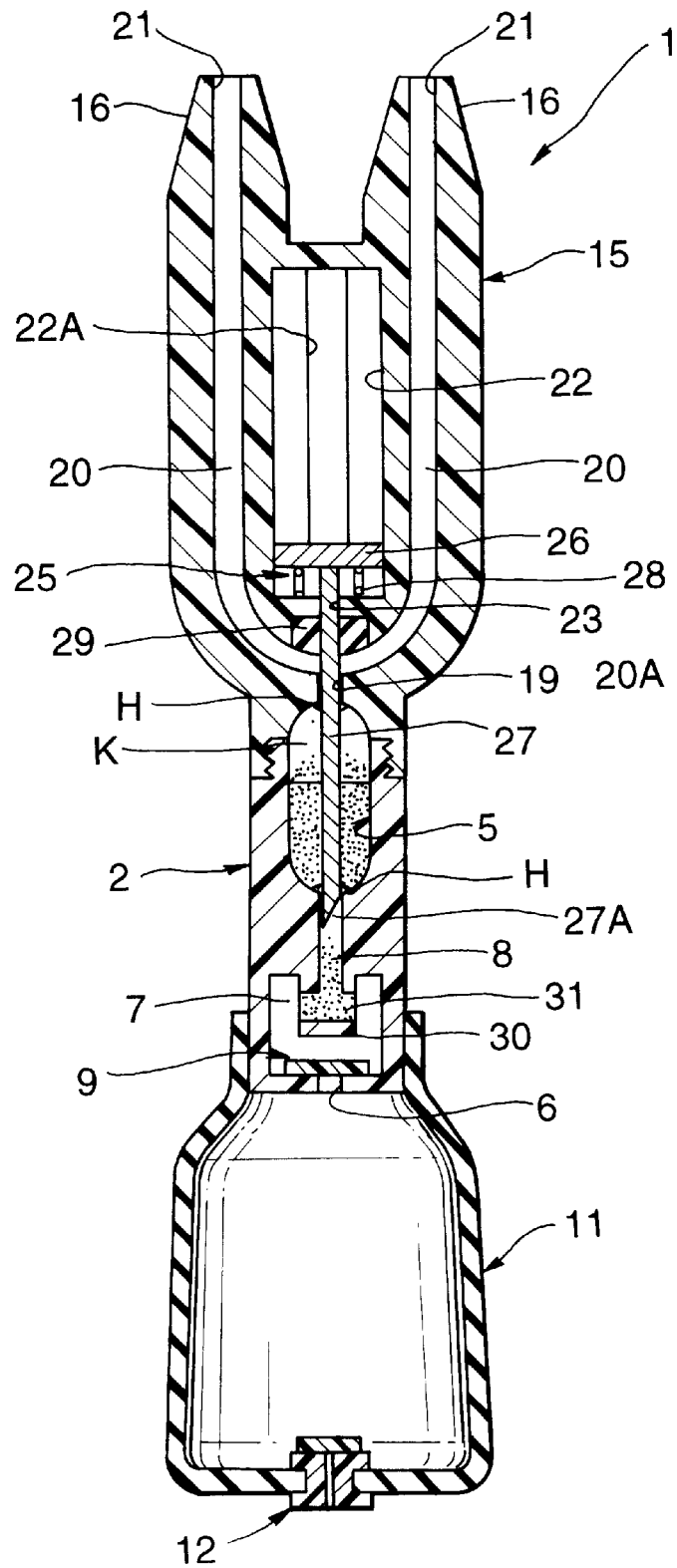
FIG. 6 is a longitudinal sectional view showing a state in which through-holes have been formed axially through the capsule with a pin of a perforator.

Here, concerning the perforator 25, by displacing each projecting section 26B of the pusher 26 along the elongate hole 22A in a direction A indicated by an arrow in FIG. 4, the hole forming section 27A of the pin 27 axially pierces the capsule K within the capsule accommodating hole 5 thereby readily forming through-holes H (See FIG. 6).

29 denotes the rubber seal installed at the seal installing step section 25 of the medicine spraying section 15. The rubber seal 29 is formed of an elastomeric material and surrounds the periphery of the hole forming section 27A of the pin 27. Accordingly, the rubber seal 29 maintains a powder-tight seal against the medicine flowing in the capsule outflow-side passage 19 and in each medicine passage 20, and is slidable relative to the pin 27, thereby preventing the medicine from penetrating through the pin inserting hole 23 into the perforator installing hole 22.

30 denotes the medicine trapping section which projects in the shape of a column having a small diameter to face the supplying valve 9, within the supplying valve chamber 7 of the capsule holder 2. The medicine trapping section 30 is formed diametrically with a trapping passage 31 through which the capsule inflow-side passage 8 and the supplying valve chamber 7 are communicated with each other. The medicine trapping section 30 is arranged such that medicine dropping to the side of the supplying valve 9 is trapped within the trapping passage 31 when the hole formation section 27A of the pin 27 pierces the capsule K during hole formation.

The medicine administering device 1 for nasal cavities, according to this embodiment is arranged as discussed above. Next, its operation during hole formation for the capsule will be discussed with reference to FIGS. 4 to 7.

Figure 5:
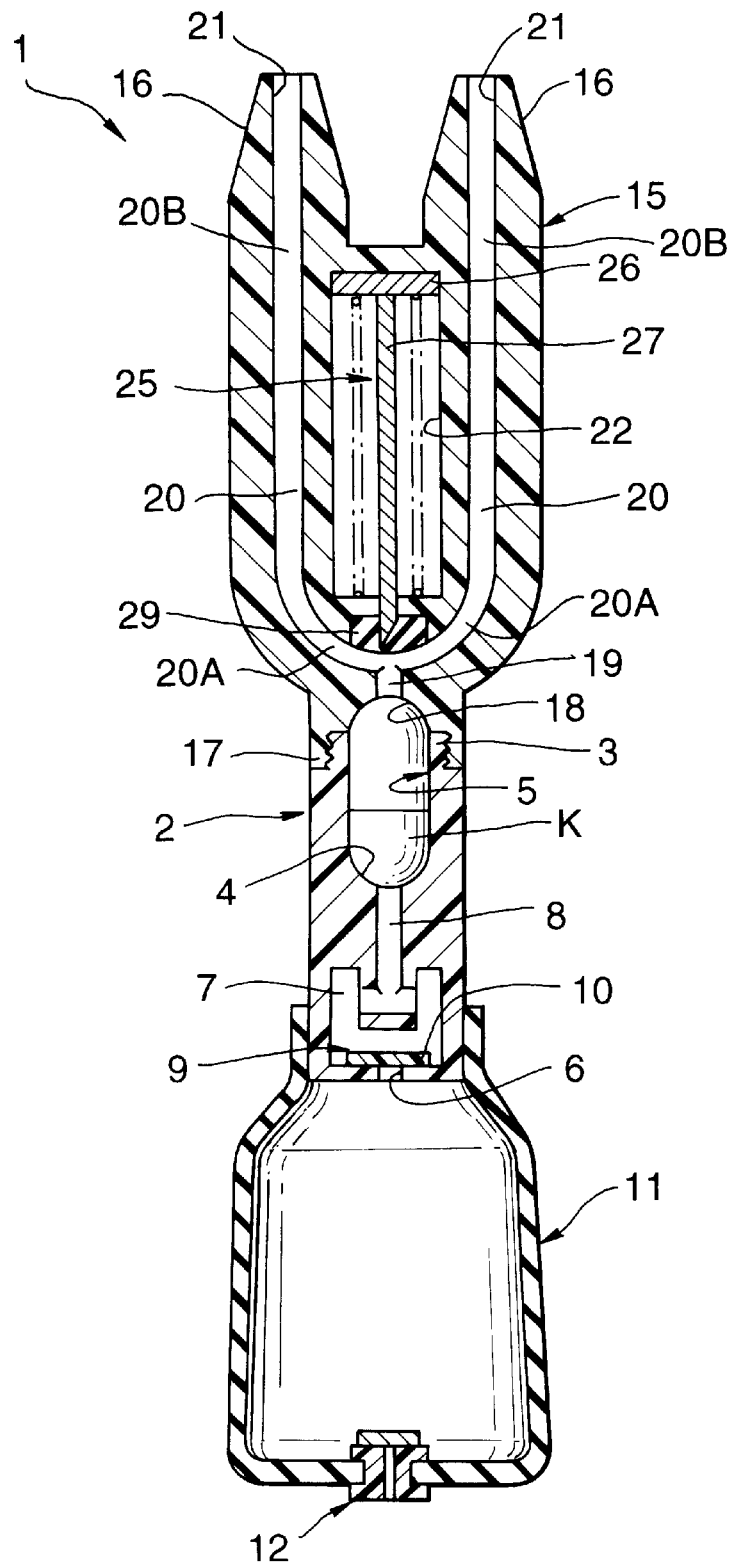
FIG. 5 is a longitudinal sectional view showing a state in which the capsule has been accommodated in the medicine administering device for nasal cavities.

First, as shown in FIG. 4, the capsule K is inserted in the one-side capsule hole 4 of the capsule holder 2, and then the external thread portion 3 of the capsule holder 2 and the internal thread portion 17 of the medicine spraying section 15 are engaged with each other so that the capsule K is accommodated within the capsule accommodating hole 5 constituted by the one-side capsule hole 4 of the capsule holder 2 and the other-side capsule hole 18 of the medicine spraying section 15 as shown in FIG. 5.

Then, as shown in FIG. 6, the respective projecting sections 26B of the pusher 26 constituting the perforator 25 are displaced toward a lower side (in a direction A indicated by the arrow in FIG. 4) by hand. By this, the hole forming section 27A of the pin 27 pierces the capsule K through the capsule outflow-side passage 19 thereby forming the through-holes H which are located at axially opposite sides. At this time, although medicine within the capsule K drops into the capsule inflow-side passage 8, this medicine can be trapped by the trapping passage 31 of the medicine trapping section 30.

Figure 7:
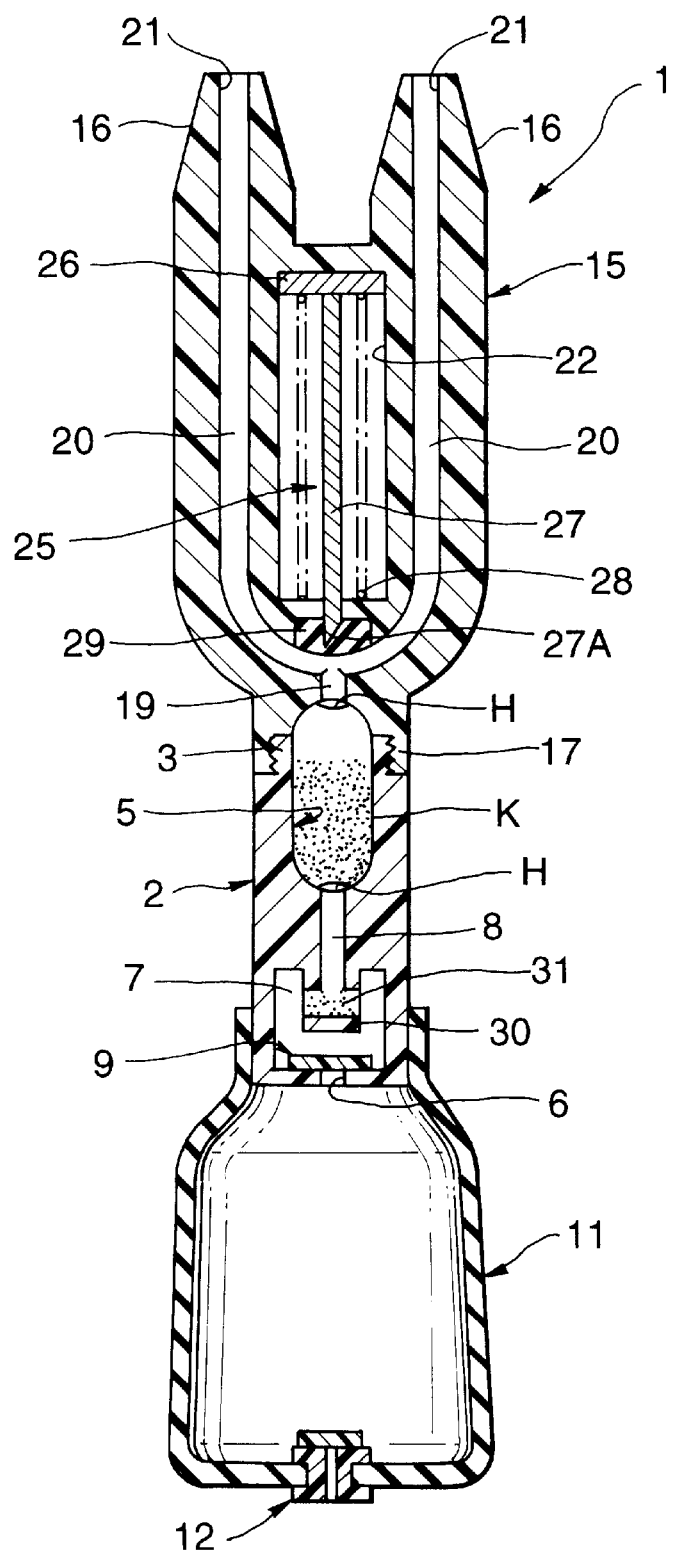
FIG. 7 is a longitudinal sectional view showing a state in which the pin is restored to its original position after the through-holes have been formed in the capsule with the pin of the perforator.

After the hole formation, the pusher 26 is automatically restored to allow the capsule outflow-side passage 19 and each medicine passage 20 to be communicated with each other under a condition in which the through-holes H are formed at the axially opposite sides of the capsule K, as shown in FIG. 7. The hole forming section 20A of the pin 27 is maintained to obtain a powder-tight seal with the rubber seal 29. As described above, the medicine dropping from the capsule K during the hole formation is trapped by the medicine trapping section 30, so that the medicine is prevented from dropping to the side of the supplying valve 9 and the pump section 11.

Thus, when the hole is formed in the administering device 1 for nasal cavities, according to this embodiment, the through-holes H can be readily formed in the axial direction of the capsule K, while the medicine that drops during the hole formation can be trapped by the medicine trapping section 30.

Figure 8:
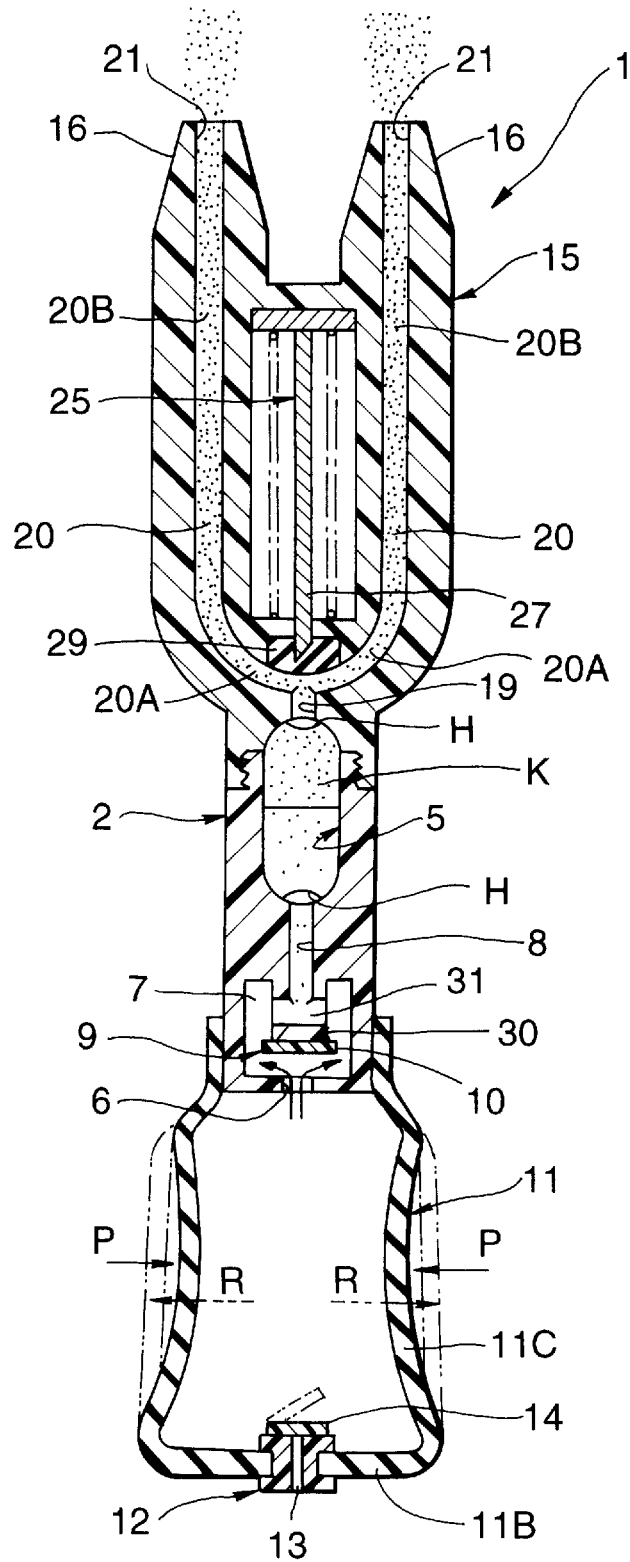
FIG. 8 is a longitudinal sectional view showing a state in which medicine within the capsule is being sprayed by pressing a pump section.
Figure 9:
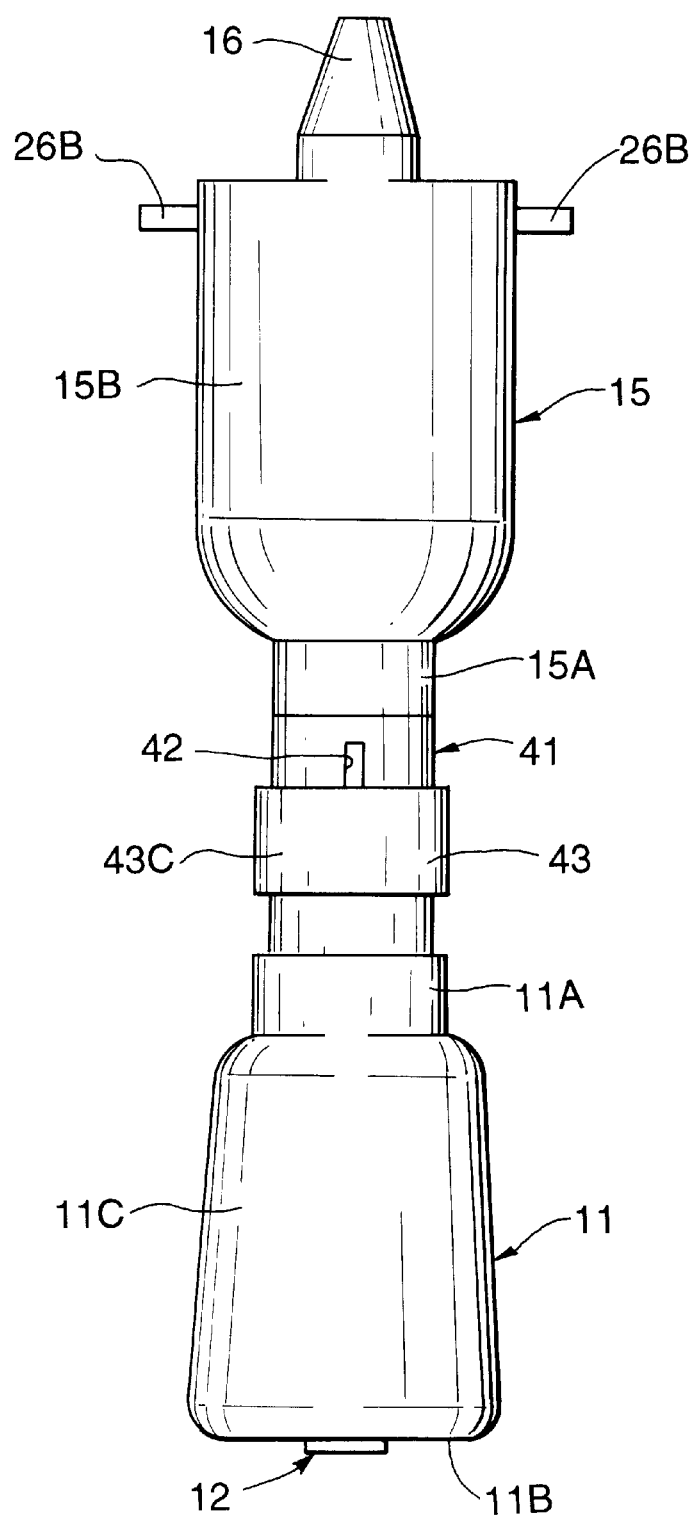
FIG. 9 is a side view showing the medicine administering device for nasal cavities, according to a second embodiment.
Figure 10:
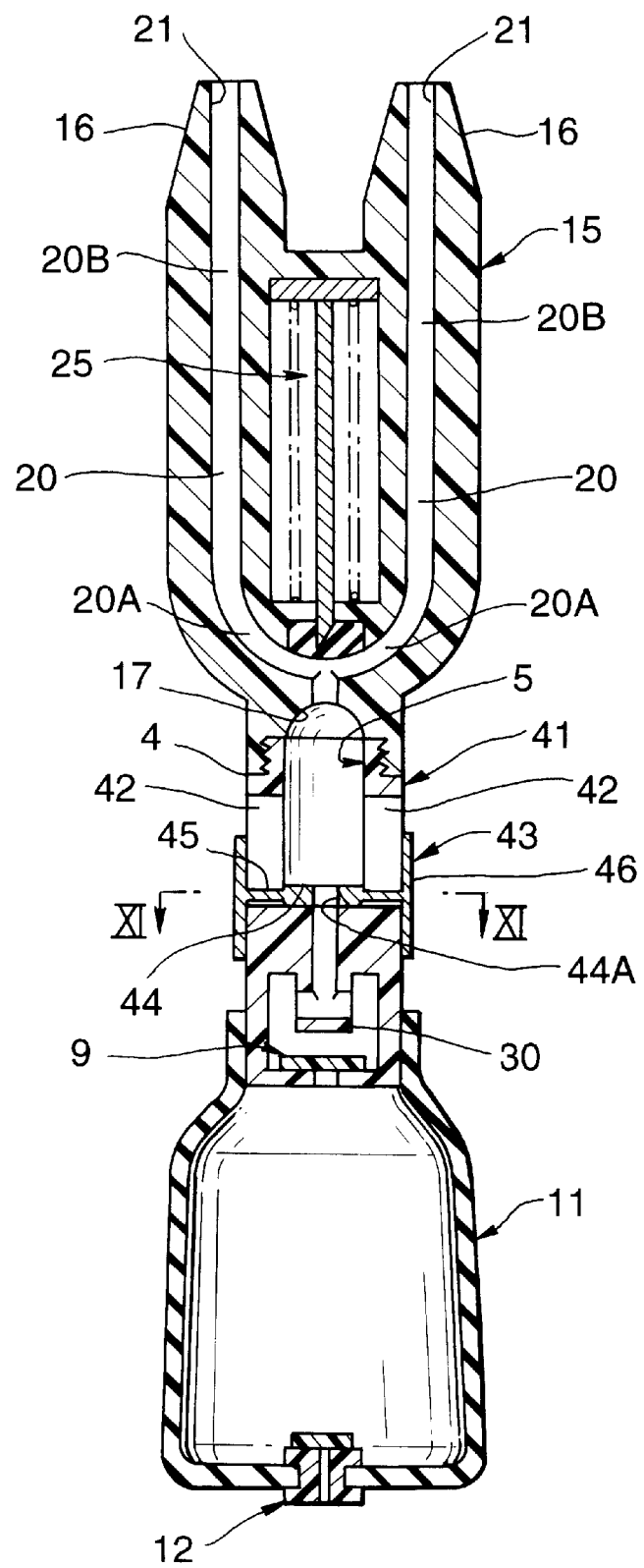
FIG. 10 is a longitudinal sectional view showing the medicine administering device for nasal cavities, according to a second embodiment of the present invention.
Figure 11:
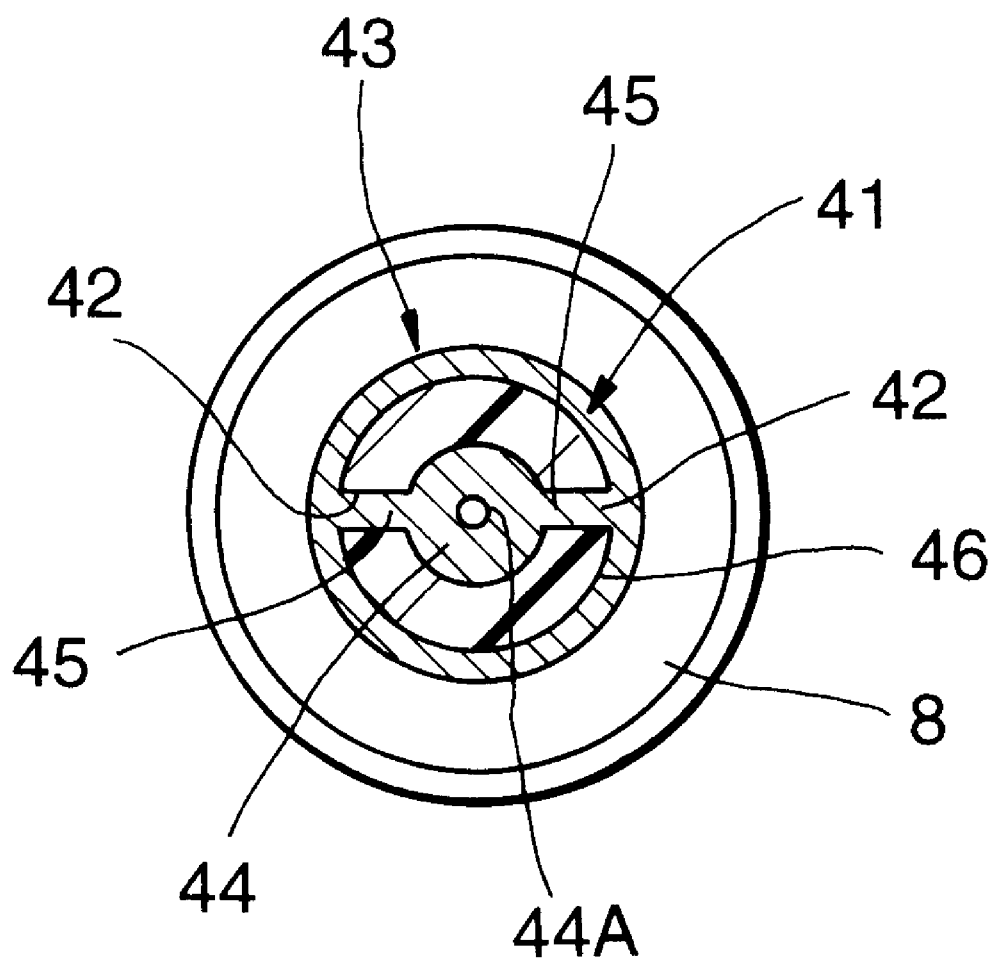
FIG. 11 is a transverse sectional view as viewed from the direction XI—XI indicated by an arrow in FIG. 10.

Referring to FIG. 8, administering the medicine to a patient will now be discussed.

First, the left and right nasal cavity inserting sections 16 of the medicine spraying section 15 are respectively inserted into the left and right nasal cavities of the patient. Then, as shown in FIG. 8, the pressing section 11C of the pump section 11 is pressed in a direction P indicated by an arrow. By this, the valve member 10 of the supplying valve 9 opens so that air is supplied from the pump section 11 toward the capsule K within the capsule holder 2.

By this, air from the pump section 11 flows from the inside of the capsule K into the nasal cavities of the patient through each medicine passage 20 and the left and right spraying holes 21. At this time, the medicine within the capsule K is stirred by air flowing in the capsule K, and then this medicine is transferred together with air to the nasal cavities of the patient.

The medicine spraying section 15 is formed with medicine passages 20, which are formed by causing the capsule outflow-side passage 19 to diverge into two parts. The nasal cavity inserting sections 16 (with the spraying holes 21) to be inserted into the left and right nasal cavities of the patient are formed respectively at the tip ends of the medicine passages 20. Accordingly, the medicine transferred together with air can be equally divided to be simultaneously administered to the left and right nasal cavities of the patient.

The straight passage section 20B is formed in each medicine passage 20, and therefore the medicine is regulated in flow and provided with straight advancing characteristics during passage through each straight passage section 20B, so that the medicine can be forcibly ejected into the nasal cavities of the patient in an accelerated state.

The axial dimension LO of the capsule accommodating hole 5 according to this embodiment is slightly smaller than the axial dimension LK of the capsule K, and therefore play of the capsule K within the accommodating hole 5 is prevented, while the inflow-side through-hole H of the capsule K tightly contacts the capsule inflow-side passage 8 and the outflow-side through-hole H of the capsule K tightly contacts the capsule outflow-side passage 19. Accordingly, air from the pump section 11 can stream into the capsule K, so that the medicine can be introduced from the through-hole H of the capsule K to the outflow-side passage 19. As a result, the amount of the medicine ejected from each spraying hole 21 can be stabilized, and therefore almost all of the medicine within the capsule K can be administered to the left and right nasal cavities of the patient by pressing the pump section 11 about three times. As a result of this operation, the patient can be free from difficulties encountered during administration.

During hole formation, the medicine trapped in the trapping passage 31 of the medicine trapping section 30 can be transferred with air so as to supply medicine within the capsule K into the left and right nasal cavities of the patient. As a result, the amount of the medicine left in the medicine administering device 1 can be reduced, so that a predetermined amount of the medicine can be accurately administered to the patient, while reducing the frequency of cleaning of the medicine administering device 1.

When the pump section 11 is restored, the supplying valve 9 closes while the valve member 14 of the sucking valve 12 opens. Accordingly, air is sucked into the pump section 11 from the outside through the sucking passage 13 so that the pressing section 11C of the pump section 11 is restored in a direction R indicated by an arrow shown in dot-dot-dash line.

In the medicine administering device 1, according to this embodiment, the medicine spraying section 15 is formed with the two medicine passages 20 diverged from the capsule outflow-side passage 19 and with the nasal cavity inserting sections 16 (the spraying holes 21) to be inserted into the left and right nasal cavities of the patient, while the axial dimension LO of the capsule accommodating hole 5 according to this embodiment is slightly smaller than the axial dimension LK of the capsule K to tightly fix the capsule K. Additionally, the inflow-side through-hole H of the capsule K is tightly contacted with the capsule inflow-side passage 8, while the outflow-side through-hole H of the capsule K is tightly contacted with the capsule outflow-side passage, so that the medicine can be introduced from the through-hole H of the capsule K to the inflow-side passage 19. Accordingly, the medicine can be administered almost equally into the nasal cavities of the patient under few administering actions during medicine administration. As a result, the medicine can be administered to the patient by pressing the pump section 11 about three times without repeating this administering action many times, alternately for left and right nasal cavities, upon inserting the medicine administering device into each nasal cavity of the patient, thus simplifying the administering action.

Since the perforator 25 is housed in the medicine spraying section 15, the through-holes H can be readily axially formed in the capsule K only by causing the pusher 26 to axially displace after the capsule K has been accommodated within the capsule accommodating hole 5. Further, since the perforator 25 is housed in the medicine spraying section 15, it may not be lost as compared with one in which a removable cap is provided with a pin. And it is safe to handle.

The capsule holder 2 is formed with the medicine trapping section 30 so that the medicine dropping during hole formation is trapped by the trapping passage 31 of this medicine trapping section 30. Since this trapped medicine is also administered together with air to the patient, the amount of the medicine to be left in the medicine administering device 1 can be reduced to nearly zero, so that the medicine filled in the capsule K can be accurately administered to the patient. Additionally, the cleaning frequency of the medicine administering device 1 for nasal cavities can be largely reduced as compared with the conventional technique.

The seal installing step section 24 of the medicine spraying section 15 is provided with a rubber seal 29 formed of elastomeric material, in which the periphery of the hole forming section 27A of the pin 27 is surrounded by the rubber seal 29. Accordingly, each medicine passage 20 and the perforator installing hole 22 are separated from each other to maintain a powder-tight seal, thereby preventing the medicine in air flowing through each medicine passage 20 from penetrating in the perforator installing hole 22.

Further, by virtue of the straight passage section 20B formed in the medicine passage 20, flow-regulating characteristics and straight advancing characteristics are provided to the medicine, so that the medicine can be forcibly ejected from respective spraying holes 21 toward the nasal cavities of the patient in an accelerated state. Accordingly, administration can be made to predetermined positions in the nasal cavities of the patient every administering action, thereby improving an absorption efficiency of the medicine in the nasal cavities of the patient.

Next, FIGS. 9 to 13 show a second embodiment, in which the feature of this embodiment resides in the fact that the capsule holding section is provided with a capsule ejecting tool. In this embodiment, the same reference numerals are assigned to the same component elements as those of the first embodiment discussed above, thereby omitting the explanation therefor.

In the figures, 41 denotes a capsule holder according to this embodiment, used in place of the capsule holder 2 discussed in the first embodiment. The capsule holder 41 is arranged generally similar to the capsule holder 2, in which slide holes 42 are formed diametrically to axially extend relative to the one-side capsule hole 4.

43 denotes the capsule ejecting tool which includes a disc section 44, which has generally the same size as the traverse cross-sectional surface of the capsule K and is formed at its central part with an inserting hole 44a through which the hole forming section 27A of the pin is to be inserted, beam sections 45 extending diametrically of the disc section 44, and a cylindrical section 46 for supporting the disc section 44 through each beam section 45. Each beam section 45 is axially movably inserted in each slide hole 42.

Subsequently, an operation of the capsule ejecting tool is shown in and will be explained with reference to FIGS. 12 and 13.

Figure 12:
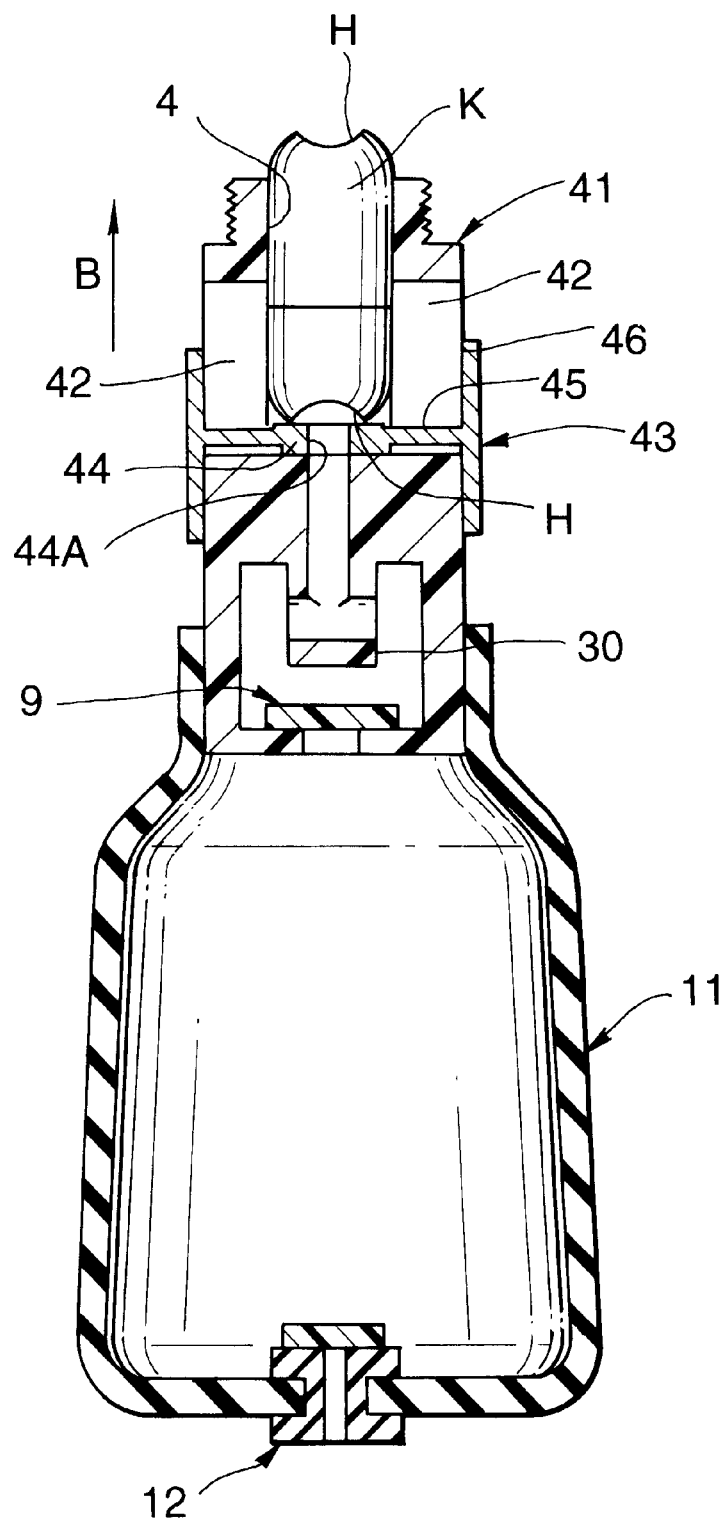
FIG. 12 is a longitudinal sectional view showing a state in which the empty capsule is accommodated in the capsule accommodating section after medicine administration.
Figure 13:
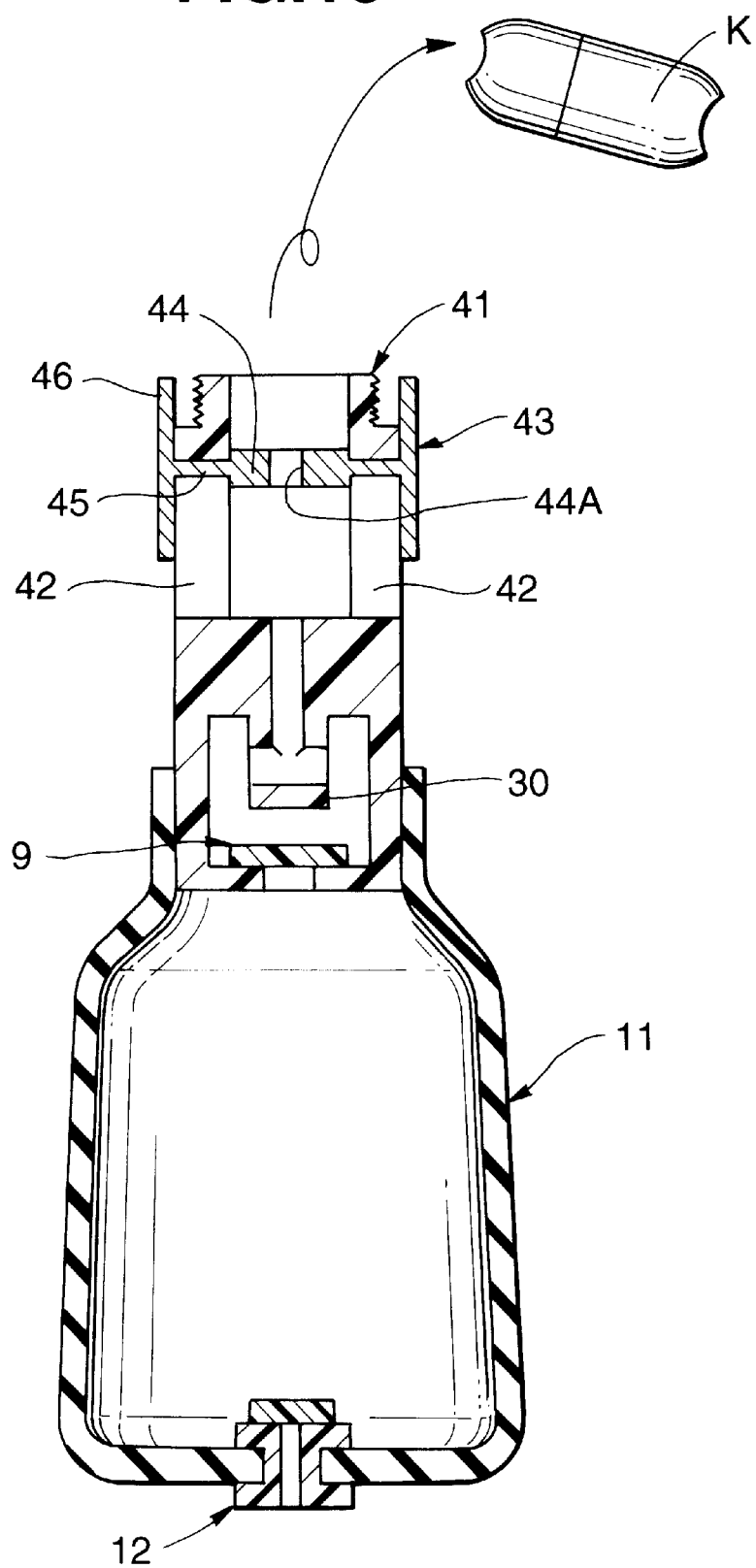
FIG. 13 is a longitudinal sectional view showing a state in which the capsule has been ejected from the capsule holding section with a capsule ejecting tool.

FIG. 12 shows a condition in which the medicine spraying section 15 is detached from the capsule holder 41 after the administration of the medicine has been completed, in which only the empty capsule K is accommodated in the one-side capsule hole 4 so that the disc section 44 of the capsule ejecting tool 43 is in contact with the lower side of the capsule K. By moving the cylindrical section 46 of the capsule ejecting tool 43 in a direction B indicated by an arrow under this condition, the capsule K is smoothly released from the one-side capsule hole 4 so that the capsule K can be readily discarded.

Also with the thus arranged medicine administering device of this embodiment, not only the same functional effects as those of the above-discussed first embodiment can be obtained but also the discarding treatment of the capsule K can be readily accomplished because the used capsule K can be readily removed, making it unnecessary to directly grasp the capsule K by hand during removal by virtue of the fact that the capsule holder 41 is provided with the capsule ejecting tool 43.

Figure 14:
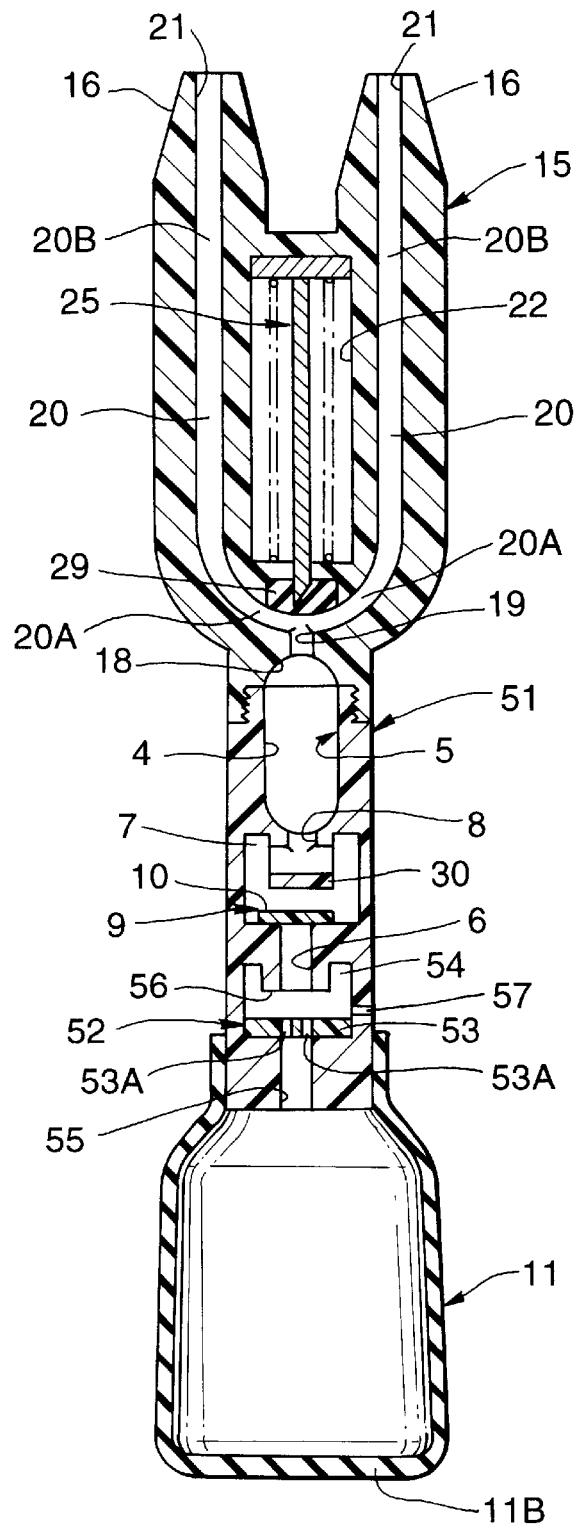
FIG. 14 is a longitudinal sectional view of the medicine administering device for nasal cavities, showing a third embodiment of the present invention.

Next, FIG. 14 shows a third embodiment. The feature of this embodiment resides in the fact that the supplying valve 9 and a sucking valve 52 are disposed between the capsule holder 51 and the pump section 11. In this embodiment, the same reference numerals are assigned to the same component elements as those of the first embodiment discussed above, thereby omitting the explanation therefor.

In the figure, 51 denotes a capsule holder used in this embodiment, in place of the capsule holder 2 in the first embodiment. The capsule holder 51 is provided at its axially middle part with the supplying valve 9 and provided at its axial one-side with the sucking valve 52, and further provided at its axial other-side with the one-side capsule hole 4.

More specifically, the supplying valve 9 is formed with the air supply passage 6 at the axial one-side of the valve member 10 and the supplying valve chamber, which has a relatively large diameter, at the axial other-side of the valve member 10. The sucking valve 52 has a valve member 53 which is disposed in a sucking valve chamber 54. The valve member 53 opens and closes at its one side a pump-side air supply passage 55, and opens and closes at the other side thereof a valve seat 56 projecting into the sucking valve chamber 54. The capsule holder 51 is formed with a communication hole 57 through which the sucking valve chamber 54 is always in communication with the atmosphere, in which the valve member 53 closes the communication passage 57 when the valve member 53 is seated on the valve seat 56.

The valve member 53 of the sucking valve 52 is formed with a plurality of small-diameter passages 53A through which the sucking valve chamber 54 and the pump-side air supply passage 55 are in communication with each other.

Here, concerning the sucking valve 52, when the pump section 11 supplies air, the valve member 53 is seated on the valve seat 56 and closes the communication passage 57, so that the air is supplied from the pump section 11 through the small-diameter passages 53A to the supplying valve 9 through the capsule inflow-side passage 8. When the pump section 11 sucks, the valve member 53 moves to the side of the pump section 11 so that air is sucked into the pump section 11 through the communication passage 57 and each small-diameter passage 53A of the valve member 9. Since the supplying valve 9 is closed, no air is sucked into the pump section 1 from the side of the capsule holder 51.

Thus, also with the medicine administering device according to this embodiment, the same functional effects as those of the above-discussed first embodiment can be obtained, while the arrangement of the pump section 11 is simplified since it is unnecessary to provide a sucking valve in the pump section 11.

Figure 15:
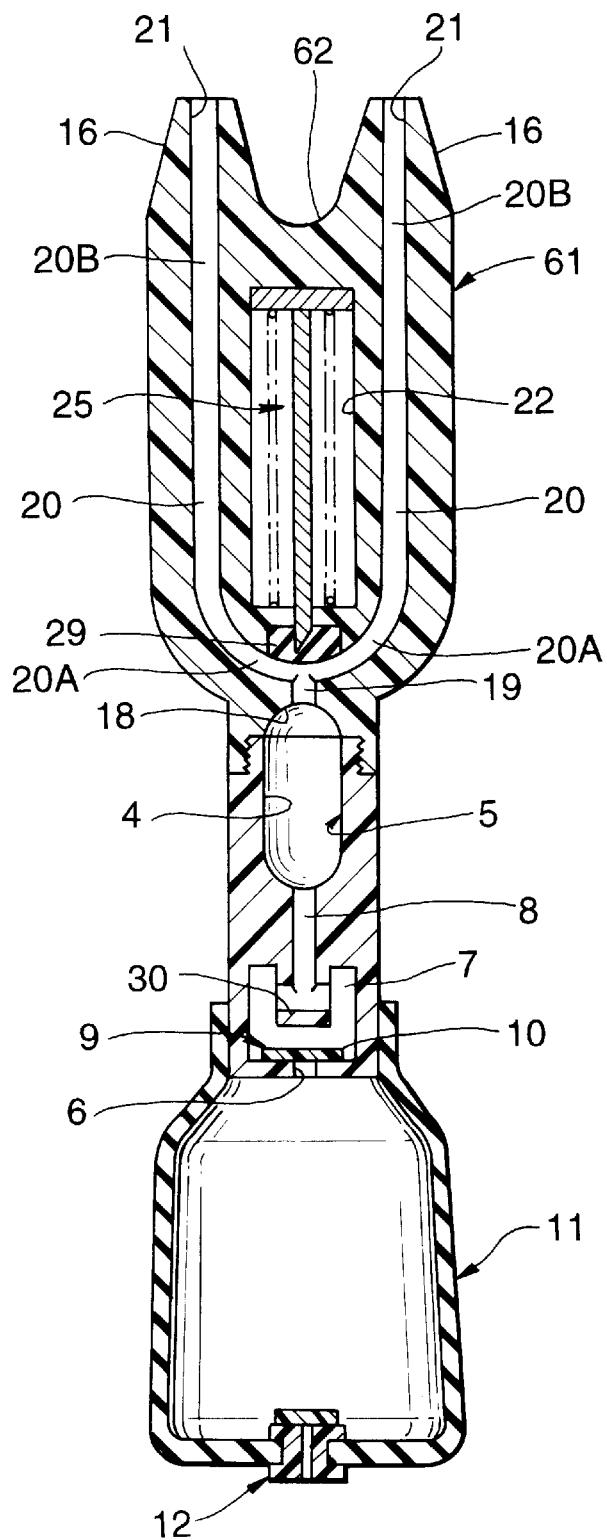
FIG. 15 is a longitudinal sectional view of the medicine administering device for nasal cavities, showing a fourth embodiment of the present invention.

Next, FIG. 15 shows a fourth embodiment. The feature of this embodiment resides in the fact that a contacting section 62 having an accuate surface is formed between the nasal cavity inserting sections 16 of the medicine spraying section 61 to come into contact with a portion between the nasal cavities of the patient. In this embodiment, the same reference numerals are assigned to the same component elements as those of the first embodiment discussed above, thereby omitting the explanation therefor.

Also with the thus arranged embodiment, not only the same functional effects as those of the above-discussed first embodiment can be obtained, but also a predetermined medicine administration can be always accomplished by omitting nonuniformity in insertion dimension of the nasal cavity inserting sections 16 into the nasal cavities by virtue of providing the contacting section 62 to which the portion between the nasal cavities of the patient is to be contacted.

Figure 16:
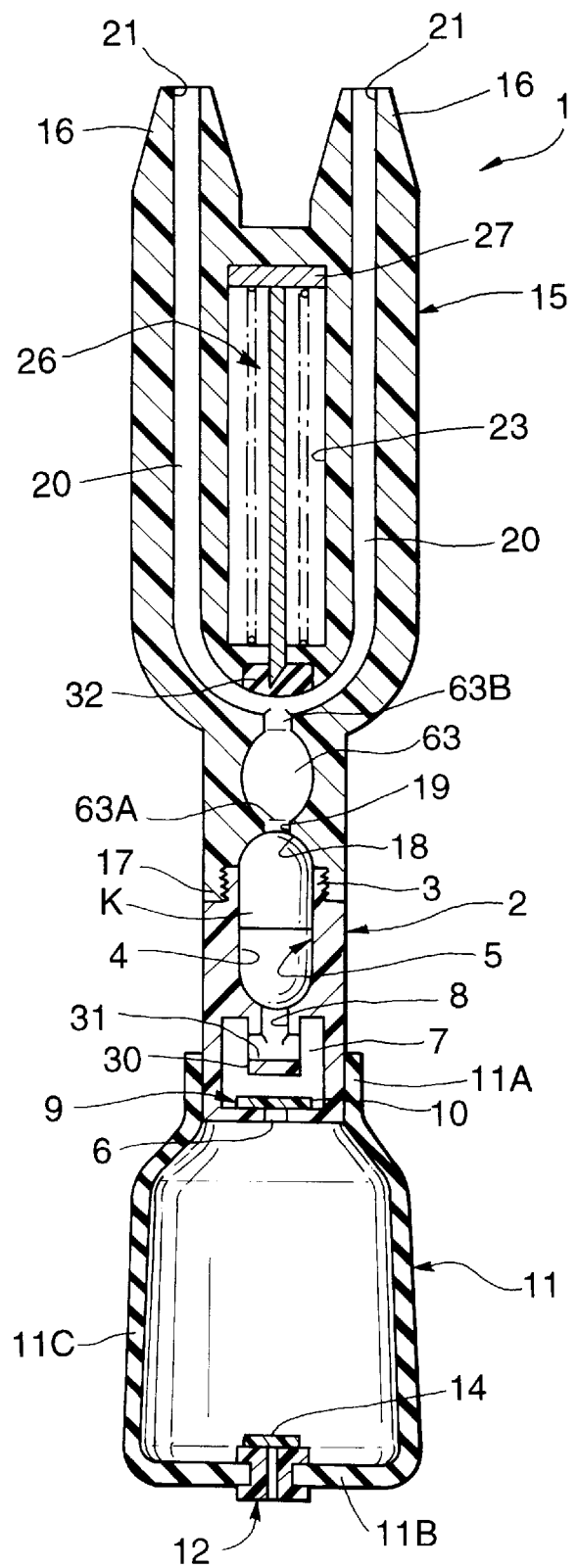
FIG. 16 is a longitudinal sectional view of the medicine administering device for nasal cavities, showing a fifth embodiment of the present invention.

FIG. 16 shows a fifth embodiment according to the present invention, in which a spreading chamber 63 is disposed in the middle part of the capsule outflow-side passage 19. More specifically, this spreading chamber 63 is formed having a larger diameter than the capsule outflow-side passage 19 in order that air and medicine can be well mixed to obtain a uniform mixing degree under the action of air flow within the spreading chamber 63 during supply of air. An inflow hole section 63A and an outflow hole section 63B have the same diametrical dimension as that of the capsule outflow-side passage 19, and are arranged to be formed by smoothly decreasing the diameter of the central part of the spreading chamber 63.

Figure 17:
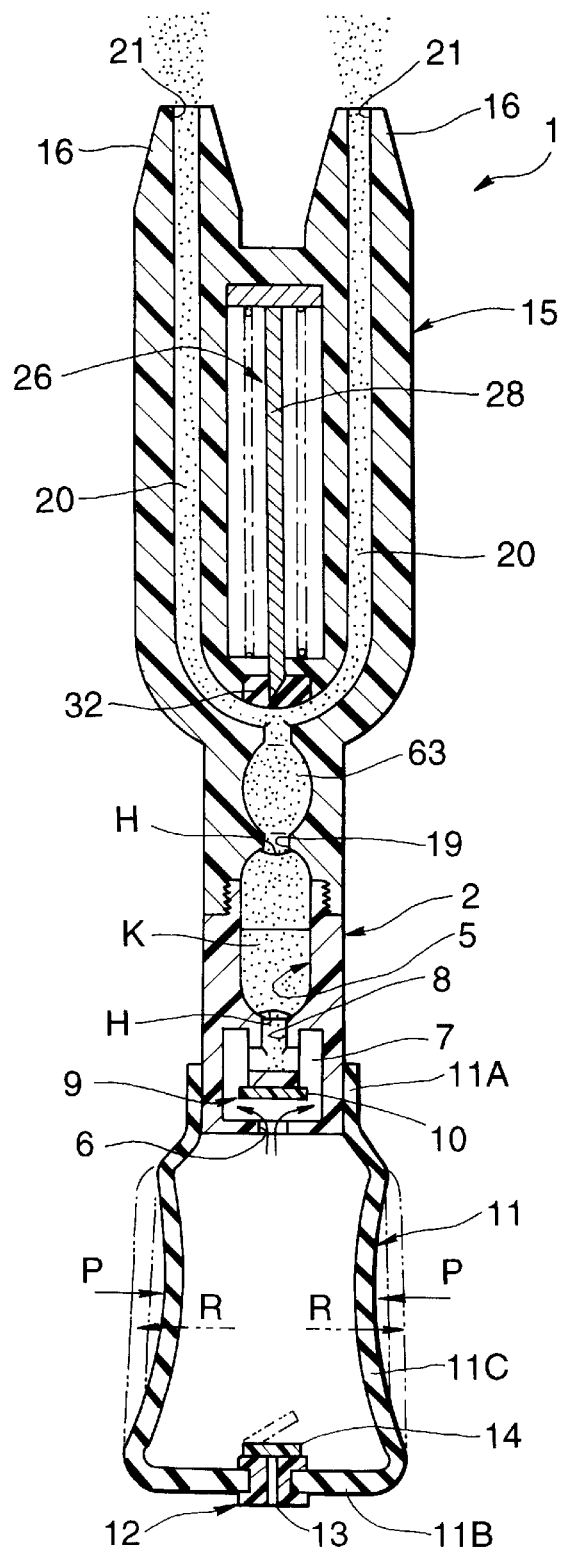
FIG. 17 is a longitudinal sectional view showing a state in which the medicine within the capsule is sprayed by pressing the pump section in the fifth embodiment.

Accordingly, when the pressing section 11c of the pump section 11 is pressed as shown in FIG. 17 upon inserting the left and right nasal cavity inserting section 16 of the medicine spraying section 15 respectively into the left and right nasal cavities of the patient after the through-holes H are axially formed in the capsule K by the perforator 26 as discussed above, the valve member 10 of the supplying valve 9 opens so that air is supplied from the pump section 1 toward the capsule holder 2.

Air from the pump section 11 flows from the inside of the capsule K into the nasal cavities of the patient through the capsule outflow-side passage 19, the spreading chamber 63, each medicine passage 20 and each spraying hole 21. At this time, the medicine within the capsule K is stirred by air flowing in the capsule K, and then this medicine is transferred together with air to the nasal cavities of the patient.

Figure 18:
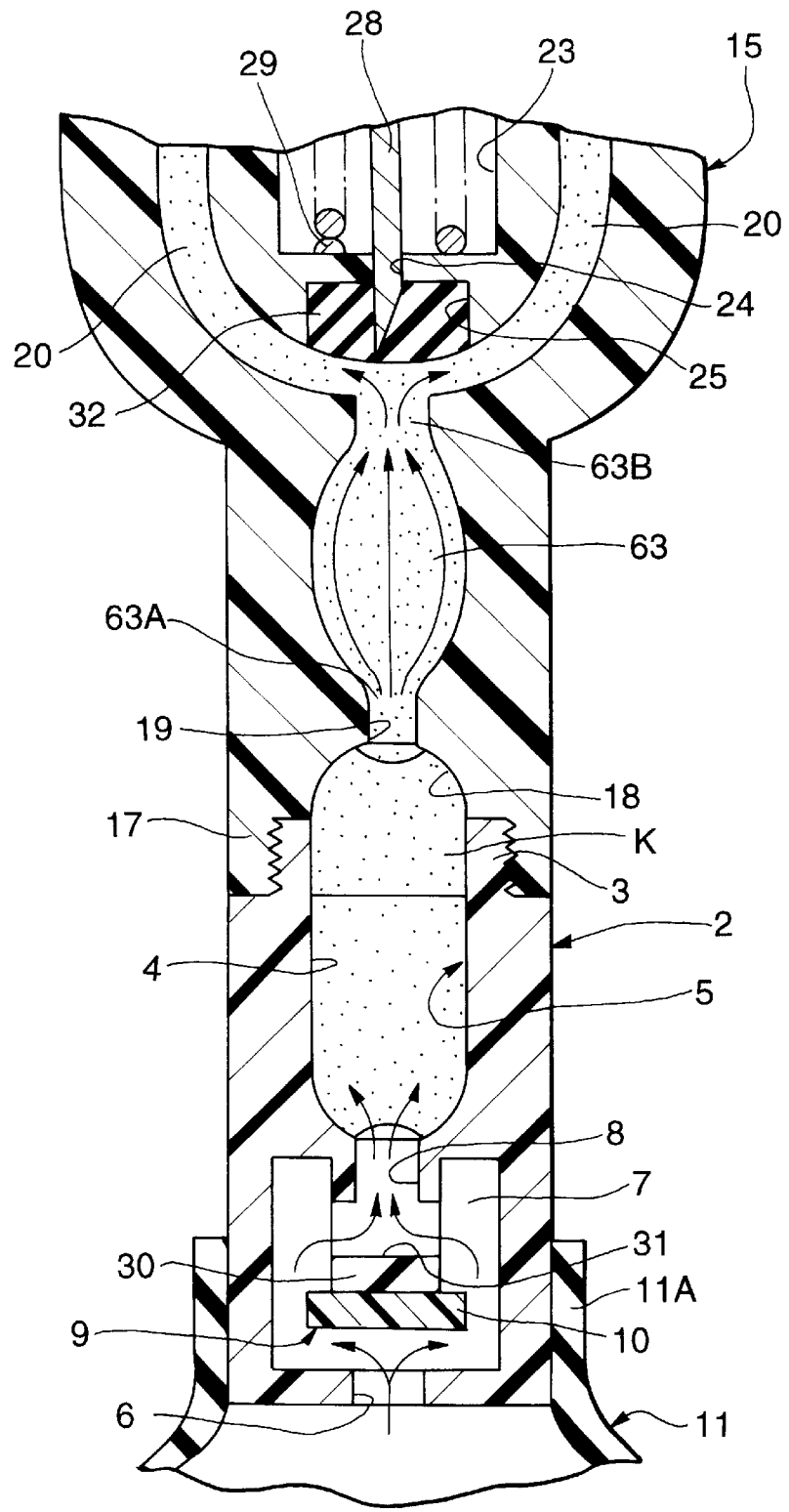
FIG. 18 is a longitudinal sectional view showing a spreading chamber in FIG. 17 in its enlarged state.

Additionally, as shown in FIG. 18, air streaming out with the medicine from the capsule K flows into the large-diameter spreading chamber 63, in which air streams collide with each other due to difference in diametrical dimension between the capsule outflow-side passage 19 and the spreading chamber 63, thereby uniformizing the mixing degree of the medicine and air. Then, air with which the medicine is uniformly mixed streams through the outflow hole section 22B to each medicine passage 20.

The medicine spraying section 15 is formed with the medicine passages 20, which are formed by causing the capsule outflow-side passage 19 to diverge into two parts. The nasal cavity inserting sections 16 (with the spraying holes 21) to be inserted into the left and right nasal cavities of the patient are formed respectively at the tip ends of the medicine passages 20. Accordingly, the medicine transferred together with air from the spreading chamber 63 can be equally divided and simultaneously administered to the left and right nasal cavities of the patient.

Figure 19:
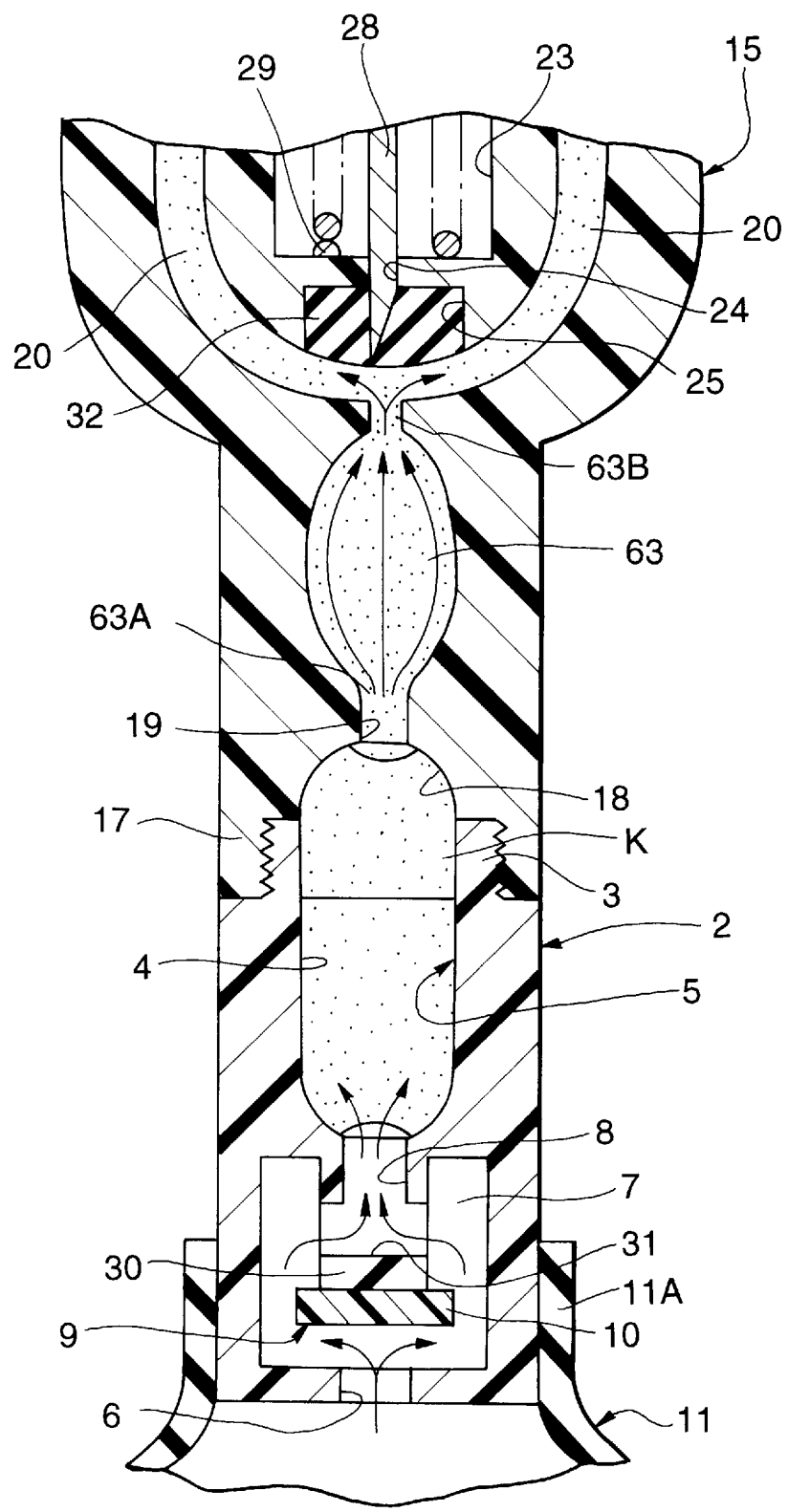
FIG. 19 is an enlarged longitudinal sectional view of the spreading chamber, showing a sixth embodiment of the present invention.

Next, FIG. 19 shows a sixth embodiment. The feature of this embodiment resides in the fact that the outflow hole section 63B of the spreading chamber 63 of the medicine spraying section 15 is formed to have a diameter smaller than that of the inflow hole section 63A. In this embodiment, the same reference numerals are assigned to the same component elements as those of the first embodiment discussed above, thereby omitting the explanation therefor.

Also with the thus arranged medicine administering device according to this embodiment, not only the same functional effects as those of the above-discussed fifth embodiment can be obtained, but also the mixing degree can be uniformized by enhancing collision of air streams within the spreading chamber 63 thereby to securely mixing air and the medicine by virtue of minimizing the diameter of the inflow hole section 63B.

Also in the fifth and sixth embodiments, the contacting section 62 having the arcuate surface may be formed between the nasal cavity inserting sections 16 of the medicine spraying section 61 to come into contact with a portion between the nasal cavities of the patient similar to that shown in FIG. 15, by which the predetermined medicine administration can be always accomplished by omitting nonuniformity in insertion dimension of the nasal cavity inserting sections 16 into the nasal cavities.

Figure 20:
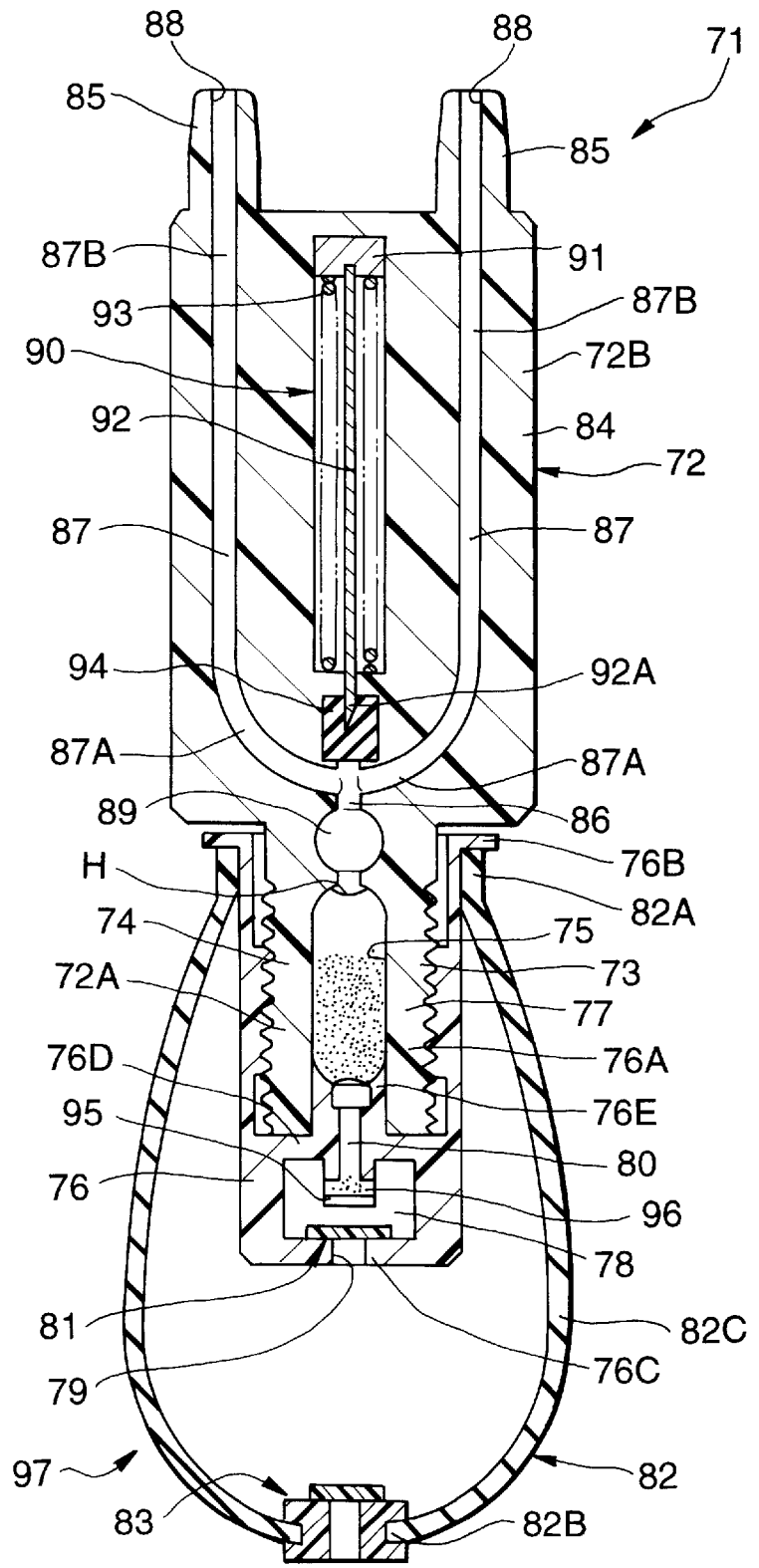
FIG. 20 is a longitudinal sectional view of the medicine administering device for nasal cavities, showing a seventh embodiment of the present invention.

FIG. 20 shows a seventh embodiment according to the present invention. The feature of this embodiment resides in the fact that the capsule accommodating section and the medicine spraying section are formed integrally, in which the pump section is assembled to the capsule accommodating section after the capsule has been accommodated in the capsule accommodating section. In this embodiment, the same reference numerals are assigned to the same component elements as those of the first embodiment discussed above, thereby omitting the explanation therefor.

In the figure, 71 denotes the medicine administering device according to this embodiment. The medicine administering device 71 for nasal cavities is generally comprised of a medicine administering device main body 72 which is formed by integrating the capsule holder 74 and the medicine spraying section 84; the pump section 82 for supplying air toward the capsule accommodated in the medicine administering device main body 72; and the perforator 90 disposed in the medicine administering device main body 72 to form through-holes in the capsule.

72 denotes the medicine administering device main body which is formed of a resin material and formed in a cylindrical shape. The axial one-side (air inflow-side) of the medicine administering device main body 72 has a small diameter section 72A which is formed at its outer peripheral surface with an external thread portion 73 which is engageable with an internal thread portion 77 of a pump holder 76. The small-diameter section 72A is arranged to serve as the capsule holder 74. The axial other-side (air outflow-side) of the medicine administering device main body 72 has a large-diameter section 72B which is arranged to serve as the medicine spraying section 84.

74 denotes the capsule holder which is formed in the small-diameter section 72A to constitute the capsule holding section. The capsule holder 74 is formed in a small-diameter cylindrical shape and formed at its inside with the capsule accommodating hole 75 which opens to the end face of the capsule holder, so that the capsule can be held within the capsule accommodating hole 75 by inserting a pressing projection 76E of a pump holder 76, after the capsule K is inserted in the capsule accommodating hole 75.

76 denotes the pump holder for holding the capsule K in the capsule accommodating hole 75. The pump holder 76 is formed in the shape of a cylinder having a closed bottom, and includes a cylindrical section 76A, an opened section 76B and a bottom section 76C. The pump holder 76 is formed with a partition wall section 76D which defines a supplying valve chamber 78 between it and the bottom section 76C, and a capsule pressing projection 76E which projects from the partition wall section 76D toward the opened section 76B to be inserted in the capsule accommodating hole 75 to support the capsule K.

The cylindrical section 76A is formed at its inner peripheral surface with an internal thread portion 77 to be engaged with the external thread portion 73. The supplying valve chamber 78 is defined between the above-mentioned bottom section 76 and the partition wall section 76D. The bottom section 76C is formed with an air supply passage 79 through which air from the pump section 82 is supplied. Further, a small-diameter capsule inflow-side passage 80 communicated with the supplying valve chamber 78 is formed throughout the above-mentioned partition wall section 76D and the capsule pressing projection 76E, in which the partition wall section 76D is formed with the medicine trapping section 95.

81 denotes the supplying valve located within the supplying valve chamber 78 of the pump holder 76 and disposed to be capable of opening and closing the air supply passage 79. The supplying valve 81 opens when air is supplied from the pump section 82, and is seated to close the air supply passage 79 when air is sucked.

82 denotes the pump section disposed at the outer periphery of the pump holder 76. The pump section 82 accommodates therein the pump holder 76. The pump section 82 is formed of a rubber material and formed in an elongate spherical shape. The pump section 82 includes an opened section 82A, a bottom section 82B and a pressing section 82C at its peripheral surface. The opened section 82A is integrally fixed to the opened section 76B of the pump holder 76 by means of welding, bonding or the like. The bottom section 82B is provided at its central portion with a sucking valve 83.

83 designates the sucking valve which is formed at the bottom section 82B of the pump section 82 and is arranged to close when air is supplied from the pump section 82 and to open to suck air from outside into the pump 82 when air is sucked.

84 denotes the medicine spraying section formed at the large-diameter section 72B of the medicine administering device main body 72. The large-diameter section 72B has a pair of nasal inserting sections 85 projecting from its end face. The medicine spraying section 84 is formed with a capsule outflow-side passage 86 in communication with the capsule accommodating hole 75 of the above-mentioned capsule holder 74, and two medicine passages 87 which extend generally in a U-shape upon diverging left and right from the capsule outflow-side passage 86. The tip end side of each medicine passage 87 constitutes an independent spraying hole 88 located in the nasal cavity inserting section 85.

Here, the above-mentioned medicine passages 87 include respectively diverging passage sections 87A, each of which diverges left or right from the capsule outflow-side passage 86, and further include respectively straight passage sections 87B, each of which extends from each diverging passage section 87A to the nasal cavity inserting section 85 so as to constitute an acceleration passage. Each straight passage section 87B is formed straight and elongated and therefore can provide flow-regulating characteristics and straight advancing characteristics to the medicine passing through the straight passage section 87B under the action of the air flow from the pump section 82, that the medicine can be forcibly ejected in an accelerated state through the spraying hole 88.

89 denotes the spreading chamber located at the middle part of the capsule outflow-side passage 86. The spreading chamber 89 has a diameter larger than that of the capsule outflow-side passage 86. The spreading chamber 89 is arranged such that air streams collide with each other in the spreading chamber 89 by virtue of the difference in diametrical dimension between it and the capsule outflow-side passage 86, so that the medicine and air can be well mixed with each other thereby obtaining a uniform mixing degree.

90 denotes the perforator disposed axially in the medicine spraying section 84. The perforator 90 includes, generally similarly to the perforator 25 discussed in connection with the above-mentioned first embodiment, a pusher 91, a pin 92 fixed to the central part of the pusher 91 and having a tip end side which extends toward the axial one-side to form an inclined cutting needle, and a spring 93 to bias the above-mentioned pusher 91 in an extending direction so as to push the above-mentioned pusher 91 toward the axial one-side.

94 denotes the rubber seal which is formed of an elastomeric material and surrounds the periphery of the hole forming section 27A of the pin 27 so as to maintain a powder-tight seal against the medicine flowing in the capsule outflow-side passage 86 and in each medicine passage 87, and is slidable relative to the pin 92.

95 denotes the medicine trapping section which projects into the supplying valve chamber 78 in such a manner as to be coaxial with the capsule pressing projection 76E and opposite to the supplying valve 81. The medicine trapping section 95 is formed diametrically with a trapping passage 96 through which the capsule inflow-side passage 80 and the supplying valve chamber 78 are communicated with each other. The medicine trapping section 95 is arranged such that medicine dropping to the side of the supplying valve 81 is trapped within the trapping passage 96 when the hole formation section 92A of the pin 92 pierces the capsule K during hole formation.

The pump holder 76 and the pump section 82 are integrated by fixing their respective opened sections 76B, 82A thereby constituting a pump unit 97 in cooperation with the supplying valve 81 and the sucking valve 83. The whole pump unit 97 is arranged to be detachable relative to the capsule holder 74 of the medicine administering device main body 72.

The medicine administering device 71 according to this embodiment is arranged as discussed above.

Insertion of the capsule K as a medicine administering preparation operation will now be discussed.

First, the medicine administering device 71 is divided into the medicine administering device main body 72 including the capsule holder 74 and the medicine spraying section 84, which are integrally formed, and the pump unit 97 including the pump holder 76, the pump section 82 and the like which are integrally formed. Subsequently, the capsule K is inserted in the capsule accommodating hole 75 of the capsule holder 74. Thereafter, the external thread portion 73 of the medicine administering device main body 72 is engaged with the internal thread portion 77 formed in the pump holder 76 in such a manner that the capsule pressing projection 76E is inserted into the capsule accommodating hole 75. By this, the capsule K can be axially held with the capsule pressing projection 76E within the capsule accommodating hole 75.

During hole formation, the through-holes H are formed in the capsule K by the hole forming section 92A of the pin 92 of the perforator 90. The medicine trapping section 95 prevents the medicine from dropping to the pump section 82.

Also during medicine administration after formation of the through-holes H, the medicine within the capsule K can be transferred to the nasal cavities of the patient under the action of air generated from the pump section 82 by pressing the pressing section 82C of the pump section 82, similarly to the above-discussed first embodiment.

Thus, with the medicine administering device 1 according to this embodiment, the medicine administering device main body 72 including the capsule holder 74 and the medicine spraying section 84 which are integrally formed, and the pump unit 97 including the pump holder 76, the pump section 82 and the like are arranged detachable from each other, so that the capsule holder 74 of the medicine administering device main body 72 is accommodated within the pump unit 97 (the pump section 82).

Accordingly, the axial dimension of the medicine administering device 71 can be minimized as compared to that of the medicine administering devices according to the other embodiments, thereby making the device relatively small in size so that the device can be readily carried.

Also in this embodiment, the straight passage sections 87B are formed respectively in the medicine passages 87, and therefore the medicine is regulated in flow and provided with straight advancing characteristics during passage through each straight passage section 87B, so that the medicine can be forcibly ejected into the nasal cavities of the patient in an accelerated state.

While the supplying valve chamber 78, the medicine trapping section 95 and the like are arranged to be integrally formed with the pump holder 76 in the above-mentioned seventh embodiment, the present invention is not limited in connection with this and therefore the respective ones may be formed separate from each other.

Additionally, while the medicine administering device main body 72 and the pump unit 97 are arranged to be assembled with each other by engaging the external thread portion 73 of the capsule holder 74 and the internal thread portion of the pump holder 76, the present invention is not limited in connection with this and therefore the lower end of the medicine spraying section 84 may be formed at its outer periphery with an engaging section while the opened section 76B of the pump holder may be formed with an engaged section so that the engaged section is engaged with the engaging section, thereby rendering the medicine administering device main body 72 and the pump unit 97 detachable from each other.

Further, while the pump unit 97 is arranged by integrally forming the pump holder 76 and the pump section 82, the pump holder 76 and the pump section 82 may be separately installed to the medicine administering device main body 72 by detachably installing the opened section 76B of the pump holder 76 to the outer periphery of the capsule holder 74 of the medicine administering device main body 72 and by fixing the opened section 82A of the pump section 82 to the outer periphery of the medicine spraying section 84 of the medicine administering device main body 72.

As discussed above, the medicine administering device for nasal cavities, according to the present invention can be applied to a device which uses not only powder-state medicine but also medicine of fine granule or the like.

We claim:

1. A medicine administering device for nasal cavities, comprising:

a capsule holding section configured to hold a capsule containing medicine, said capsule holding section having a capsule accommodating hole in which the capsule is accommodated;

a pump section configured to connect to said capsule holding section to supply air to the capsule in said capsule holding section;

a medicine spraying section connected to said capsule holding section and having first and second medicine passages having respective tip ends serving as independent spraying holes, to spray the medicine within the capsule into left and right nasal cavities of a patient under the action of air supplied from said pump section; and a perforator including a pin configured to be movable to form a through-hole in the capsule within said capsule holding section, wherein said medicine spraying section has a third medicine passage positioned between said first and second medicine passages of said medicine spraying section and said accommodating hole of said capsule holding section, said first and second medicine passages diverging from said third medicine passage, said pin of said perforator being insertable through said third medicine passage.

2. A medicine administering device for nasal cavities, as claimed in claim 1, wherein an axial dimension of the accommodating hole is slightly smaller than an axial dimension of the capsule.

3. A medicine administering device for nasal cavities, as claimed in claim 1, further comprising a medicine trapping section between said capsule holding section and said pump section to trap the medicine when the through-hole is formed in the capsule by the pin of said perforator.

4. A medicine administering device for nasal cavities, as claimed in claim 1, further comprising a seal material disposed in said medicine spraying section to maintain a medicine-tight seal when said pin is inserted into said third medicine passage.

5. A medicine administering device for nasal cavities, as claimed in claim 1, further comprising a capsule ejecting tool configured to be accepted in said capsule holding section in a manner to be axially displaceable.

6. A medicine administering device for nasal cavities, as claimed in claim 1, wherein said first and second medicine passages of said medicine spraying section have straight sections arranged as acceleration passages.

7. A medicine administering device for nasal cavities, as claimed in claim 1, wherein said perforator is configured to be axially movable in said medicine spraying section.

8. A medicine administering device for nasal cavities, as claimed in claim 1, further comprising a spreading chamber disposed between the accommodating hole of said capsule holding section and said first and second medicine passages of said medicine spraying section.

9. A medicine administering device for nasal cavities, as claimed in claim 8, wherein said spreading chamber has an air outflow-side which is formed as a small-diameter hole section.

10. A medicine administering device for nasal cavities, as claimed in claim 7, wherein said medicine spraying section is formed of a material having an elasticity.

11. A medicine administering device for nasal cavities, as claimed in claim 2, further comprising a spreading chamber disposed between the accommodating hole of said capsule holding section and said first and second medicine passages of said medicine spraying section.

* * * * *

UNITED STATES PATENT AND TRADEMARK OFFICE
CERTIFICATE OF CORRECTION

PATENT NO. : 5,901,703
DATED : May 11, 1999
INVENTOR(S) : Hisatomo OHKI et al.

It is certified that error appears in the above-identified patent and that said Letters Patent is hereby corrected as shown below:

On the title page:

Please delete "[22] PCT Filed: Feb. 6, 1995" and insert the following information therefor:
--[22] PCT Filed: Feb. 6, 1996--

Signed and Sealed this

Fifth Day of September, 2000

Attest:

Attesting Officer

Q. TODD DICKINSON
Director of Patents and Trademarks